United States Patent [19]
Bennett

[11] Patent Number: 5,955,555
[45] Date of Patent: *Sep. 21, 1999

[54] POLYMERIZATION OF ETHYLENE

[75] Inventor: Alison Margaret Anne Bennett, Wilmington, Del.

[73] Assignee: E.I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/991,372

[22] Filed: Dec. 16, 1997

Related U.S. Application Data

[60] Provisional application No. 60/033,656, Dec. 17, 1996.

[51] Int. Cl.$^6$ ..................................................... C08F 4/70
[52] U.S. Cl. ........................ 526/133; 526/161; 526/129; 526/130; 526/160; 526/171; 526/172; 526/131; 526/120; 526/134; 526/352
[58] Field of Search ..................... 526/133, 161, 526/171, 129, 130, 160, 172, 120, 131, 134

[56] References Cited

U.S. PATENT DOCUMENTS

| | | | |
|---|---|---|---|
| 5,286,589 | 2/1994 | Go et al. | 430/58 |
| 5,714,556 | 2/1998 | Johnson et al. | 526/135 |

FOREIGN PATENT DOCUMENTS

| | | | |
|---|---|---|---|
| 89-045712 | 10/1989 | Japan | H01G 9/20 |
| 2-078663 | 3/1990 | Japan | C07D 213/53 |
| WO 96/37523 | 11/1996 | WIPO | C08F 10/00 |

OTHER PUBLICATIONS

L. Sacconi, et al., High–spin Five–co–ordinate Nickel(II) and Cobalt(II) Complexes with 2,6–Diacetylpyridinebis(imines), *J. Chem. Soc.*, A, 1510–1515, 1968.

Paul E. Figgins, et al., Complexes of Iron (II), Cobalt(II) and Nickel(II) with Biacetyl–bis–methylimine, 2–Pyridinal–m–ethylimine and 2,6–Pyridindial–bis–methylimine, *J. Am. Chem. Soc.*, 82, 820–824, Feb. 20, 1960.

Thomas W. Bell, et al., Molecular Architecture. 1. Sodium, Potassium, and Strontium Complexes of a Hexaazamacrocycle, an 18–Crown–6/Torand Analogue, *J. Am. Chem. Soc.*, 113, 3115–3122, 1991.

Francis Lions, et al., Tridentate Chelate Compounds. I, *J. Am. Chem. Soc.*, 79, 2733–2738, Jun. 5, 1957.

PCT/US97/23556 International Search Report dated May 13, 1998.

Reinhard Nesper, et al., Palladium (II) complexes of chiral tridentate nitrogen pybox ligands, *Journal of Organometallic Chemistry*, vol. 1, No. 507, 85–101, 1996.

*Primary Examiner*—Mark Nagumo
*Assistant Examiner*—David W. Wu
*Attorney, Agent, or Firm*—Joel D. Citron; Craig H Evans

[57] ABSTRACT

Ethylene may be polymerized by contacting it with certain iron or cobalt complexes of selected 2,6-pyridinecarboxaldehydebis(imines) and 2,6-diacylpyridinebis(imines). The polymers produced are useful as molding resins. Novel 2,6-pyridinecarboxaldehydebis (imines) and 2,6-diacylpyridinebis(imines), and novel complexes of 2,6-pyridinecarboxaldehydebis(imines) and 2,6-diacylpyridinebis(imines) with iron and cobalt are also disclosed.

45 Claims, 3 Drawing Sheets

POLYMERIZATION OF ETHYLENE

This application claims the benefit of U.S. Provisional Application No. 60/033,656, filed Dec. 17, 1996.

FIELD OF THE INVENTION

Selected iron and cobalt complexes of 2,6-pyridinecarboxaldehydebis(imines) and 2,6-diacylpyridinebis(imines) are catalysts for the polymerization of ethylene. Also disclosed herein are novel 2,6-pyridinecarboxaldehydebis(imines) and 2,6-diacylpyridinebis(imines), and cobalt and iron complexes of such compounds.

FIELD OF THE INVENTION

Polymers of ethylene are important items of commerce, millions of tons being produced annually. These polymers are used in a myriad of ways, from low molecular weight polyethylene (PE) being used as a lubricant and mold release, to higher molecular weight grades being used for fiber, films, molding resins, etc. In most cases, ethylene is polymerized using a catalyst, often a transition metal compound or complex. These catalysts vary in cost per unit weight of PE produced, the structure of the polymer produced, the possible need to remove the catalyst from the PE, the toxicity of the catalyst, etc. Due to the commercial importance of polymerizing ethylene, new polymerization catalysts are constantly being sought.

L. Sacconi, et al., J. Chem. Soc. (A), 1968 p. 1510–1515 report the synthesis of certain cobalt complexes of 2,6-diacetylpyridinebis(imines). None of these cobalt complexes or the 2,6-diacetylpyridinebis(imines) disclosed in this reference are claimed herein.

P. E. Figgins, et al., J. Am. Chem. Soc., vol. 82, p. 820–824, and/or F. Lions, et al., J. Am. Chem. Soc., vol. 79, p. 2733–2738 report the synthesis of certain 2,6-diacetylpyridinebis(imines) and certain iron and cobalt complexes of these tridentate ligands. The structures of the tridentate ligands reported in these references is different from those claimed herein, and all of the iron and cobalt complexes contain 2 molecules of the 2,6-diacetylpyridinebis(imines).

Japanese Patent Application 89-045,712 reports the compound

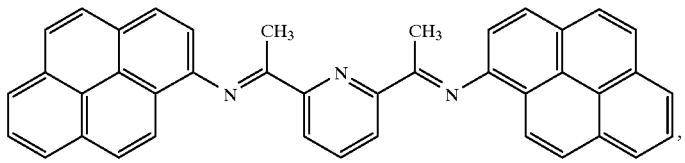

T. W. Bell, et al., J. Am. Chem. Soc., vol. 113, p. 3115–3122 (1991) reports the compound

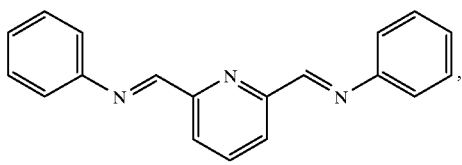

and Japanese Patent Application 02-078,663 reports the compound

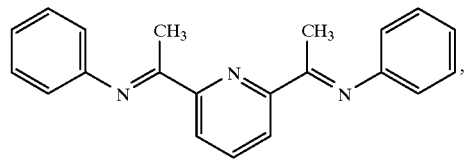

and an iron[II] complex of this latter compound in which two molecules of the 2,6-diacetylpyridinebis(imine) are present in the complex. None of these compounds are claimed herein.

SUMMARY OF THE INVENTION

This invention concerns a first process for the polymerization of ethylene, comprising, contacting, at a temperature of about −100° C. to about +200° C., a compound of the formula

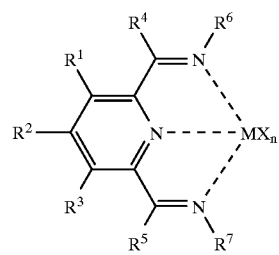

(II)

with ethylene and:

(a) a first compound W, which is a neutral Lewis acid capable of abstracting $X^-$ and alkyl group or a hydride group from M to form $WX^-$, $(WR^{20})^-$ or $WH^-$ and which is also capable of transferring an alkyl group or a hydride to M, provided that $WX^-$ is a weakly coordinating anion; or (b) a combination of second compound which is capable of transferring an alkyl or hydride group to M and a third compound which is a neutral Lewis acid which is capable of abstracting $X^-$, a hydride or an alkyl group from M to form a weakly coordinating anion;

wherein:

M is Co or Fe;

each X is an anion;

n is 1, 2 or 3 so that the total number of negative charges on said anion or anions is equal to the oxidation sate of a Fe or Co atom present in (II);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ and $R^7$ are aryl or substituted aryl; and $R^{20}$ is alkyl.

Also disclosed herein is a compound of the formula

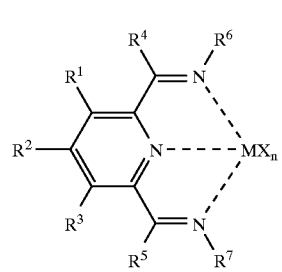
(II)

wherein:

M is Co or Fe;

each X is an anion;

n is 1, 2 or 3, so that the total number of negative charges on said anion or anions is equal to the oxidation state of a Fe or Co atom present in (II);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ is

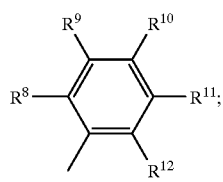
(X)

$R^7$ is

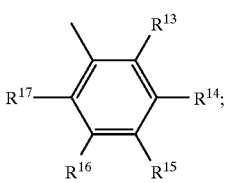
(XI)

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

This invention includes a compound of the formula

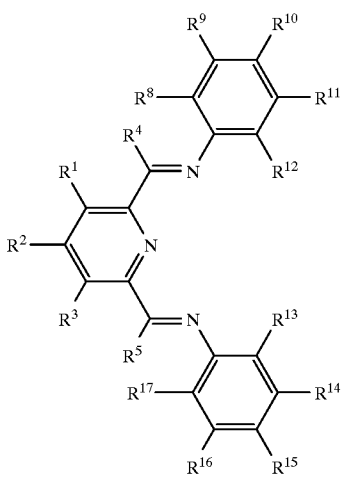
(III)

wherein:

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^8$, $R^{12}$, $R^{13}$ and $R^{17}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

This invention also concerns a second process for the polymerization of ethylene, comprising contacting, at a temperature of about −100° C. to about +200° C., a Co[II], Co[III], Fe[II] or Fe[III] complex of a tridentate ligand of the formula

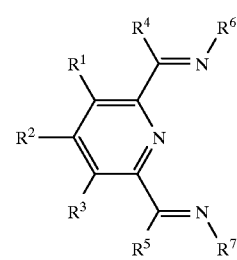
(I)

with ethylene, wherein:

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl; and $R^6$ and $R^7$ are aryl or substituted aryl;

and provided that a Co[II], Co[III], Fe[II] or Fe[III] atom also has bonded to it an empty coordination site or a ligand that may be displaced by said ethylene, and a ligand that may add to said ethylene.

This invention also includes a compound of the formula

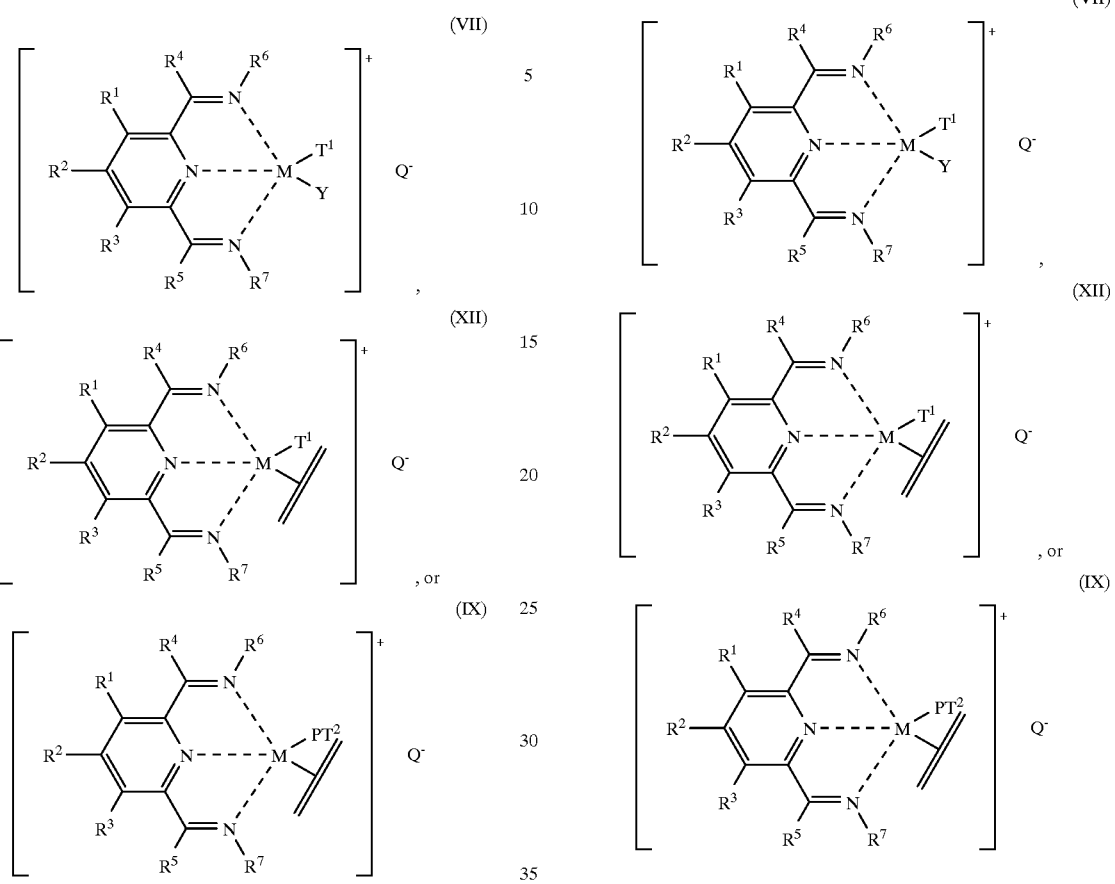

wherein:

M is Co or Fe;

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ and $R^7$ are aryl or substituted aryl;

$T^1$ is hydride or alkyl or any other anionic ligand into which ethylene can insert;

Y is a neutral ligand capable of being displaced by ethylene or a vacant coordination site;

Q is a relatively non-coordinating anion;

P is a divalent (poly)ethylene group of the formula —$(CH_2CH_2)_x$— wherein x is an integer of 1 or more; and $T^2$ is an end group.

This invention also concerns a third process for the polymerization of ethylene, comprising, contacting, at a temperature of about −100° C. to about +200° C., ethylene and a compound of the formula

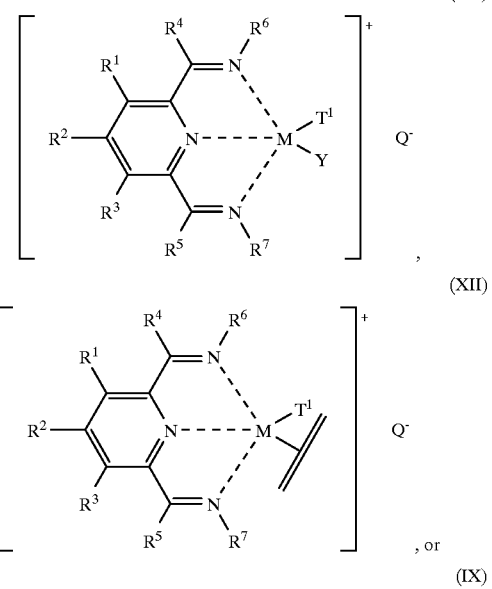

wherein:

M is Co or Fe;

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl; and $R^6$ and $R^7$ are aryl or substituted aryl;

$T^1$ is hydride or alkyl or any other anionic ligand into which ethylene can insert;

Y is a neutral ligand capable of being displaced by ethylene or a vacant coordination site;

Q is a relatively non-coordinating anion;

P is a divalent (poly)ethylene group of the formula —$(CH_2CH_2)_x$— wherein x is an integer of 1 or more; and $T^2$ is an end group.

DETAILS OF THE INVENTION

Figure 1:
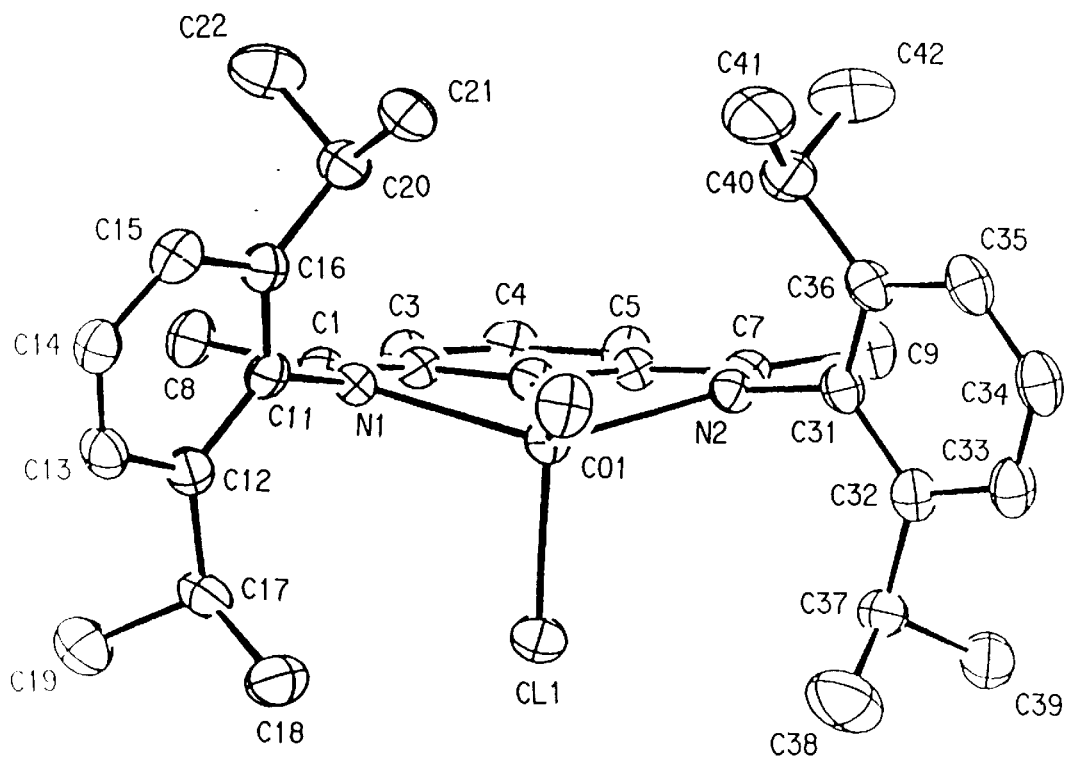
FIGS. 1, 2 and 3 are three different views of the X-ray crystallographic structure of the compound made in Example 7.

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{18}$ wherein $R^{18}$ is hydrocarbyl or substituted hydrocarbyl. In cases in which the functional group may be near a cobalt or iron atom, such as $R^4$, $R^5$, $R^8$, $R^{12}$, $R^{13}$, and $R^{17}$ the functional group should not coordinate to the metal atom more strongly than the groups in compounds containing $R^4$, $R^5$, $R^8$, $R^{12}$, $R^{13}$, and $R^{17}$ which are shown as coordinating to the metal atom, that is they should not displace the desired coordinating group.

By an "alkyl aluminum compound" is meant a compound in which at least one alkyl group is bound to an aluminum atom. Other groups such as alkoxide, hydride, and halogen may also be bound to aluminum atoms in the compound.

By "neutral Lewis base" is meant a compound, which is not an ion, which can act as a Lewis base. Examples of such compounds include ethers, amines, sulfides, and organic nitrites.

By "cationic Lewis acid" is meant a cation which can act as a Lewis acid. Examples of such cations are sodium and silver cations.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Stares, Chem. Rev., vol. 93, p. 927–942 (1993), both of which are hereby included by reference. Among such anions are those formed from the aluminum compounds in the immediately preceding paragraph and $X^-$, including $R^{19}_3AlX^-$, $R^{19}_2AlClX^-$, $R^{19}AlCl_2X^-$, and "$R^{19}AlOX^-$", wherein $R^{19}$ is alkyl. Other useful noncoordinating anions include $BAF^-$ {BAF=tetrakis[3,5-bis(trifluoromethyl)phenyl]borate}, $SbF_6^-$, $PF_6^-$, and $BF_4^-$, trifluoromethanesulfonate, p-toluenesulfonate, $(R_fSO_2)_2N^-$, and $(C_6F_5)_4B^-$.

By an empty coordination site is meant a potential coordination site that does not have a ligand bound to it. Thus if an ethylene molecule is in the proximity of the empty coordination site, the ethylene molecule may coordinate to the metal atom.

By a ligand that may add to ethylene is meant a ligand coordinated to a metal atom into which an ethylene molecule (or a coordinated ethylene molecule) may insert to start or continue a polymerization. For instance, this may take the form of the reaction (wherein L is a ligand):

Note the similarity of the structure on the left-hand side of this equation to compound (IX) (see below).

Compounds useful as ligands herein in iron and cobalt complexes are diimines of 2,6-pyridinedicarboxaldehyde or 2,6-diacylpyridines of the general formula

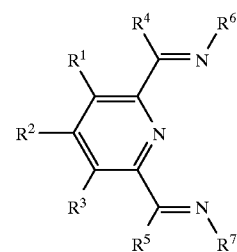

(IV)

wherein $R^1$, $R^2$ and $R^3$ are each independently hydrogen, hydrocarbyl, substituted hydrocarbyl, or an inert functional group, $R^4$ and $R^5$ are each independently hydrogen, hydrocarbyl, an inert functional group or substituted hydrocarbyl, and $R^6$ and $R^7$ are aryl or substituted aryl.

(IV) may be made by the reaction of a compound of the formula

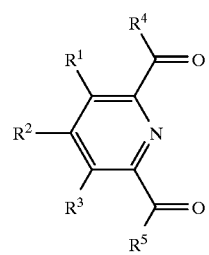

(VI)

with a compound of the formula $H_2NR^6$ or $H_2NR^7$, wherein $R^1$, $R^2$ and $R^3$ are each independently hydrogen, hydrocarbyl, substituted hydrocarbyl, or an inert functional group, $R^4$ and $R^5$ are each independently hydrogen, hydrocarbyl or substituted hydrocarbyl, $R^4$ and $R^5$ are each hydrocarbyl or substituted hydrocarbyl, and $R^6$ and $R^7$ are aryl or substituted aryl. These reactions are often catalyzed by carboxylic acids, such as formic acid. Reactions such as these are described in Examples 1–6.

Preferred compounds of formula (IV) and compounds in which (IV) is a ligand are those of compound (III) [note that (III) is a subset of (IV)], whether present in compounds such as (I), (II), (IV), (VII), (IX) and (XII). In (III), and hence in (I), (II), (IV) (VII), (IX) and (XII) that match the formula of (III), it is preferred that:

$R^1$, $R^2$ and $R^3$ are hydrogen; and/or $R^1$ and $R^3$ are hydrogen and $R^2$ is trifluoromethyl; and/or $R^9$, $R^{10}$, $R^{11}$, $R^{14}$, $R^{15}$ and $R^{16}$ is each independently halogen, alkyl containing 1 to 6 carbon atoms, or hydrogen, and it is more preferred that each of these is hydrogen; and/or $R^{10}$ and $R^{15}$ are methyl; and/or $R^8$ and $R^{13}$ is each independently halogen, phenyl or alkyl containing 1 to 6 carbon atoms, and it is it especially preferred that each $R^8$ and $R^{13}$ is alkyl containing 1–6 carbon atoms, and it is more preferred that $R^8$ and $R^{13}$ are i-propyl or t-butyl (but both $R^8$ and $R^{12}$ or both $R^{13}$ and $R^{17}$ can't be t-butyl in the same compound);

$R^{12}$ and $R^{17}$ is each independently halogen, phenyl, hydrogen, or alkyl containing 1 to 6 carbon atoms, and it is especially preferred that each $R^{12}$ and $R^{17}$ is alkyl containing 1–6 carbon atoms, and it is more preferred that $R^{12}$ and $R^{17}$ are i-propyl;

$R^4$ and $R^5$ are each independently halogen, thioalkyl, hydrogen or alkyl containing 1 to 6 carbon atoms, and it is especially preferred that $R^4$ and $R^5$ are each independently hydrogen or methyl.

Also in (III), and hence in (I), (II), (IV) (VII), (IX) and (XII) that match the formula of (III), it is preferred that:

$R^6$ is

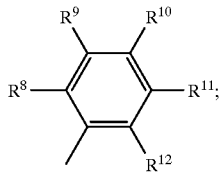
(X)

$R^7$ is

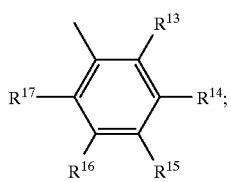
(XI)

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

Specific preferred compounds (III) [and also in (I), (II), (IV), (VII), (IX) and (XII)] are:

$R^1$, $R^2$, $R^3$, $R^9$, $R^{11}$, $R^{14}$ and $R^{16}$ are hydrogen, and $R^4$, $R^5$, $R^8$, $R^{10}$, $R^{12}$, $R^{13}$, $R^{15}$ and $R^{17}$ are methyl;

$R^1$, $R^2$, $R^3$, $R^9$, $R^{10}$, $R^{11}$, $R^{14}$, $R^{15}$ and $R^{16}$ are hydrogen, $R^8$ and $R^{13}$ are chloro, and $R^4$, $R^5$, $R^{12}$ and $R^{17}$ are methyl;

$R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are phenyl;

$R^1$, $R^2$, $R^3$, $R^4$, $R^5$, $R^9$, $R^{10}$, $R^{11}$, $R^{14}$, $R^{15}$, and $R^{16}$ are hydrogen, and $R^8$, $R^{12}$, $R^{13}$ and $R^{17}$ are i-propyl;

$R^1$, $R^2$, $R^3$, $R^9$, $R^{10}$, $R^{11}$, $R^{14}$, $R^{15}$ and $R^{16}$ are hydrogen, $R^4$ and $R^5$ are methyl, and $R^8$, $R^{12}$, $R^{13}$ and $R^{17}$ are i-propyl;

$R^1$, $R^2$, $R^3$, $R^9$, $R^{10}$, $R^{11}$, $R^{14}$, $R^{15}$ and $R^{16}$ are hydrogen, $R^4$ and $R^5$ are methylthio (CH$_3$S—), and $R^8$, $R^{12}$, $R^{13}$ and $R^{17}$ are i-propyl;

$R^1$, $R^2$, $R^3$, $R^9$, $R^{10}$, $R^{11}$, $R^{14}$, $R^{15}$ and $R^{16}$ are hydrogen, $R^4$ and $R^5$ are 1-imidazolyl, and $R^8$, $R^{12}$, $R^{13}$ and $R^{17}$ are i-propyl;

$R^1$, $R^3$, $R^9$, $R^{10}$, $R^{11}$, $R^{14}$, $R^{15}$ and $R^{16}$ are hydrogen, $R^4$ and $R^5$ are methyl, $R^2$ is trifluoromethyl, and $R^8$, $R^{12}$, $R^{13}$ and $R^{17}$ are i-propyl; and $R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are t-butyl.

In the polymerization processes described herein, it can be seen from the results that it is preferred that there be at least some steric crowding caused by the tridentate ligand about the Co or Fe atom. Therefore, it is preferred that groups close to the metal atom be relatively large. It is relatively simple to control steric crowding if (III) is the tridentate ligand, since control of steric crowding can be achieved simply by controlling the size of $R^8$, $R^{12}$, $R^{13}$ and $R^{16}$. These groups may also be part of fused ring systems, such as 9-anthracenyl.

In the first polymerization process it is preferred that X is chloride, bromide and tetrafluoroborate. It is also preferred that M is Fe[II], Fe[III], or Co[II].

In the first polymerization process described herein an iron or cobalt complex (II) is contacted with ethylene and a neutral Lewis acid W capable of abstracting $X^-$, hydride or alkyl from (II) to form a weakly coordinating anion, and must alkylate or be capable of adding a hydride ion to the metal atom, or an additional alkylating agent or an agent capable of adding a hydride anion to the metal atom must be present. The neutral Lewis acid is originally uncharged (i.e., not ionic). Suitable neutral Lewis acids include $SbF_5$, $Ar_3B$ (wherein Ar is aryl), and $BF_3$. Suitable cationic Lewis acids or Bronsted acids include NaBAF, silver trifluoromethanesulfonate, $HBF_4$, or $[C_6H_5N(CH_3)_2]^+$ $[B(C_6F_5)_4]^-$. In those instances in which (II) (and similar catalysts which require the presence of a neutral Lewis acid or a cationic Lewis or Bronsted acid), does not contain an alkyl or hydride group already bonded to the metal atom, the neutral Lewis acid or a cationic Lewis or Bronsted acid also alkylates or adds a hydride to the metal or a separate alkylating or hydriding agent is present, i.e., causes an alkyl group or hydride to become bonded to the metal atom.

It is preferred that $R^{20}$ contains 1 to 4 carbon atoms, and more preferred that $R^{20}$ is methyl or ethyl.

For instance, alkyl aluminum compounds (see next paragraph) may alkylate (II). However, not all alkyl aluminum compounds may be strong enough Lewis acids to abstract $X^-$ or an alkyl group from the metal atom. In that case a separate Lewis acid strong enough to do the abstraction must be present. For instance, in Example 37, polymethylaluminoxane is used as the "sole" Lewis acid, it both alkylates and does the abstraction from the metal atom. In Examples 60 and 61 triethylaluminum alkylates the metal atom, but is not a strong enough Lewis acid to abstract an anion from the metal atom, so another (stronger) Lewis acid, $B(C_6F_5)_3$, was also added to the polymerization. Without the stronger Lewis acid $B(C_6F_5)_3$ present, the polymerization does not proceed.

A preferred neutral Lewis acid, which can alkylate the metal, is a selected alkyl aluminum compound, such as $R^{19}_3Al$, $R^{19}AlCl_2$, $R^{19}_2AlCl$, and "$R^{19}AlO$" (alkylaluminoxanes), wherein $R^{19}$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $C_2H_5AlCl_2$, and $[(CH_3)_2CHCH_2]_3Al$.

Metal hydrides such as $NaBH_4$ may be used to bond hydride groups to the metal M.

In the second polymerization process described herein a cobalt or iron complex of (I) is either added to the polymerization process or formed in situ in the process. In fact, more than one such complex may be formed during the course of the process, for instance formation of an initial complex and then reaction of that complex to form a living ended polymer containing such a complex.

Examples of such complexes which may be formed initially in situ include

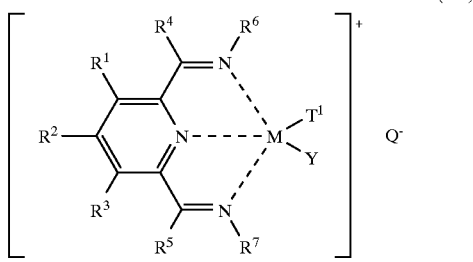

(VII)

and

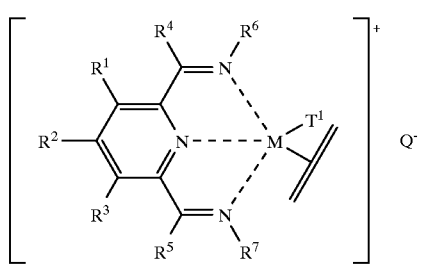

(XII)

wherein $R^1$ through $R^7$, and M are as defined above, $T^1$ is hydride or alkyl or any other anionic ligand into which ethylene can insert, Y is a neutral ligand capable of being displaced by ethylene or a vacant coordination site, the "parallel lines" are an ethylene molecule coordinated to the metal, and Q is a relatively non-coordinating anion. Complexes may be added directly to the process or formed in situ. For instance, (VII) may be formed by the reaction of (II) with a neutral Lewis acid such as an alkyl aluminum compound. Another method of forming such a complex in situ is adding a suitable iron or cobalt compound such cobalt [II] acetylacetonate (see Example 18), (I) and an alkyl aluminum compound. Other metal salts in which anions similar to acetylacetonate are present, and which may be removed by reaction with the Lewis or Bronsted acid. For instance metal halides and carboxylates (such as acetates) may be used, particularly if they are slightly soluble in the process medium. It is preferred that these precursor metal salts be at least somewhat soluble in the process medium.

After the ethylene polymerization has started, the complex may be in a form such as

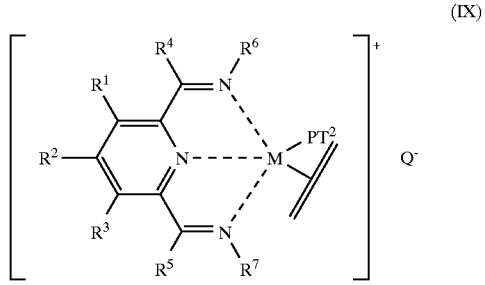

(IX)

wherein $R^1$ through $R^7$, M, and Q are as defined above, and P is a divalent (poly)ethylene group of the formula —$(CH_2CH_2)_x$— wherein x is an integer of 1 or more, and $T^2$ is an end group, for example the groups listed for $T^1$ above. Those skilled in the art will note that (IX) is in essence a polymer containing a so-called living end. It is preferred that M be in +2 oxidation state in (VII), (VIII) and (IX). Compounds such as (VII), (IX) and (XII) may or may not be stable away from an environment similar to that of the polymerization process, but they may be detected by NMR spectroscopy, particularly one or both of $^1H$ and $^{13}C$ NMR, and particularly at lower temperatures. Such techniques, especially for polymerization "intermediates" of these types are known, see for instance World Patent Application 96/23010, especially Examples 197–203, which is hereby included by reference.

(VII), (IX) and (XII) may also be used, in the absence of any "co-catalysts" or "activators" to polymerize ethylene in a third polymerization process. Except for the ingredients in the process, the process conditions for the third process, such as temperature pressure, polymerization medium, etc., may be the same as for the first and second polymerization processes, and preferred conditions for those processes are also preferred for the third polymerization process.

In all the polymerization processes herein, the temperature at which the ethylene polymerization is carried out is about −100° C. to about +200° C., preferably about −60° C. to about 150° C., more preferably about −50° C. to about 100° C. The ethylene pressure at which the polymerization is carried out is not critical, atmospheric pressure to about 275 MPa being a suitable range.

The polymerization processes herein may be run in the presence of various liquids, particularly aprotic organic liquids. The catalyst system, ethylene, and polyethylene may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene and benzene.

The ethylene polymerizations herein may also initially be carried out in the solid state [assuming (II), (III) (IV) or (VII) is a solid] by, for instance, supporting (II), (III) (IV) or (VII) on a substrate such as silica or alumina, activating it with the Lewis (such as W, for instance an alkylaluminum compound) or Bronsted acid and exposing it to ethylene. The support may also be able to take the place of the Lewis or Bronsted acid, for instance an acidic clay such as montmorillonite. Another method of making a supported catalyst is to start a polymerization or at least make an iron or cobalt complex of another olefin or oligomer of an olefin such as cyclopentene on a support such as silica or alumina. These "heterogeneous" catalysts may be used to catalyze polymerization in the gas phase or the liquid phase. By gas phase is meant that the ethylene is transported to contact with the catalyst particle while the ethylene is in the gas phase. Preparations of these types of heterogeneous catalysts are found in Examples 43–46.

In all of the polymerization processes described herein oligomers and polymers of ethylene are made. They may range in molecular weight from oligomeric olefins (see Example 32, which is mostly decenes), to lower molecular weight polyethylene oils and waxes, to higher molecular weight polyethylenes. One preferred product is a polymer with a degree of polymerization (DP) of about 10 or more, preferably about 40 or more. By "DP" is meant the average number of repeat (monomer) units in a polymer molecule.

In the Examples, the pressures given are gauge pressures. The following abbreviations and terms are used:

Branching—reported as the number of methyl groups per 1000 methylene groups in the polymer. Not corrected for end groups. It is determined by $^1H$ NMR.

Dispersity—weight average molecular weight divided by number average molecular weight (Mn).

DSC—differential scanning calorimetry
FW—formula weight
GC—gas chromatography
GPC—gel permeation chromatography
ΔH—heat of fusion (of polyethylene)
Mn—number average molecular weight
MeOH—methanol
PMAO—polymethylaluminoxane
RT—room temperature
THF—tetrahydrofuran
Tm—melting point
Turnover #—the number of moles of ethylene polymerized per mole of cobalt or iron compound present.

Structures were determined by X-ray crystallography using a Rigaku RU300 instrument with an R-AXIS image plate detector using MoKα radiation. The structure was solved by direct methods (SHELXS or MULTAN), using a refinement by full-matrix least squares on F.

Metals analyses of heterogeneous catalysts were performed by Inductively Coupled Plasma Atomic Absorption (ICP) analysis.

In the Examples, the apparatus for polymerization run at about 34.5 kPa ethylene pressure were run in Schlenk tubes. In general the metal complex (or metal compound and ligand) was dissolved or slurried in dry "solvent" under nitrogen. The stoppered flask was then brought to the desired reaction temperature, flushed well with ethylene, placed under a pressure of about 34.5 kPa of ethylene and stirred vigorously. The other catalyst component(s) were then added and the polymerization was allowed to proceed.

Polymerizations run at higher pressures were done in a Parr® 100 ml stirred autoclave. The procedure was similar to that used in the Schlenk tubes (above).

EXAMPLE 1

2,6-Diacetylpyridinebis(2,4,6-trimethylphenylimine)

In a 200 mL round bottom flask, 5.0 g of 2,6-diacetylpyridine (FW 163.18, 0.0306 mole) and 75 mL of methanol were placed. Next 8.28 g of 2,4,6-trimethylaniline (FW 135.21, 0.0612 mole) and three drops of formic acid were added and the solution stirred at RT under nitrogen for 16 h, at which time a yellow precipitate was observed. This was filtered off and washed with cold methanol. Collected 5.42 g (44.5% yield) of a yellow solid which was recrystallized from methanol with a minimum amount of methylene chloride to yield 4.10 g of the pure title compound. The filtrate was placed in the original flask and stirred for 1 day. More yellow precipitate appeared which was filtered off and washed with cold methanol. Collected 3.63 g (another 29.8% yield). This material was recrystallized to yield 3.11 g of yellow crystals. $^1$H-NMR (ppm, CDCl$_3$): 2.2 (s, 12H), 2.25 (s, 6H), 2.3 (s, 6H), 6.9 (s, 4H), 7.9 (t, 1H), 8.5 (d, 2H).

EXAMPLE 2

2,6-Diacetylpyridinebis(2-chloro-6-methylphenylimine)

In a 200 mL round bottom flask, 2.0 g of 2,6-diacetylpyridine (FW 163.18, 0.0122 mole) and 50 mL of methanol were placed. Next, 3.45 g of 2-chloro-6-methylaniline (FW 141.60, 0.0245 mole) was added followed by three drops of formic acid and the solution was stirred at RT under nitrogen for four d, at which time no precipitate had formed. The reaction was then refluxed for 24 h. GC analysis indicated that reaction was incomplete. Refluxing was continued for a total of 1 week. Solvent was stripped from the reaction mixture via rotovap. Flash chromatography through a basic alumina column (eluted with hexane/ethyl acetate 20:1) lead to isolation of an oil. The oil was then crystallized from methanol/methylene chloride. Collected 0.21 g (4.2% yield) of pale yellow crystals. $^1$H-NMR (ppm, CDCl$_3$): 2.12 (s, 6H), 2.32 (s, 6H), 6.95 (t, 2H), 7.13 (d, 2H), 7.30 (d, 2H), 7.92 (t, 1H), 8.5 (d, 2H).

EXAMPLE 3

2,6-Diacetylpyridinebis(2-biphenylimine)

In a 100 mL round bottom flask, 0.48 g of 2,6-diacetylpyridine (FW 163.18, 0.00295 moles), 1.0 g of 2-aminobiphenyl (FW 169.23, 0.0059 moles), and 20 mL of methanol were placed. Three drops of formic acid were added and the resulting solution stirred under nitrogen. A precipitate formed after one day. This was filtered off, washed with cold methanol and dried. Collected 0.84 g (61% yield) of pale yellow solid. $^1$H NMR (ppm, CDCl$_3$): 2.15 (s, 6H), 6.8 (d, 2H), 7.15–7.50 (m, 16H), 7.75 (t, 1H), 8.10 (d, 2H).

EXAMPLE 4

2,6-Pyridinedicarboxaldehydebis(2,6-diisopropylphenylimine)

In a 35 mL round bottom flask, 0.28 g of 2,6-pyridinedicarboxaldehyde (FW 135.12, 0.00207 moles), 0.73 g of 2,6-diisopropylaniline (FW 177.29, 0.00414 moles), and 15 mL of methanol were placed. Three drops of formic acid were added and the solution stirred. A precipitate formed within 5 min. Stirring was continued overnight. The solid was filtered off, washed with cold methanol and dried. Collected 0.86 g (91.5% yield) of a pale yellow solid. $^1$H NMR (ppm, CDCl$_3$), 1.2 (d, 24H), 3.0 (m, 4H), 7.0–7.2 (m, 6H), 8.0 (t, 1H), 8.35 (s, 2H), 8.4 (d, 2H).

EXAMPLE 5

2,6-Diacetylpyridinebis(2,6-diisopropylphenylimine)

In a 200 mL round bottom flask, 2.0 g of 2,6-diacetylpyridine (FW 163.18, 0.0122 moles) was placed in 50 mL of methanol. Next, 4.32 g of 2,6-diisopropylaniline (FW 177.29, 0.0244 moles) and 3 drops of formic acid were added. The solution was stirred at RT overnight. The next morning a white precipitate had formed. Stirring was continued for one more day before filtering off the solid, washing with cold methanol and drying. Collected 3.63 g (61.8% yield) of a pale yellow solid. NMR revealed that both the monoimine and diimine product were present.

The solid was then placed in a flask with 200 mL methanol and the methanol was brought to a boil. The solid was not soluble, so chloroform was added to the hot stirring mixture until the solid went into solution. A further 4.50 g of 2,6-diisopropylaniline was then added and the solution heated to 50° C. After a total of 7 d of heating, a precipitate formed which was filtered, washed with cold methanol, and dried. Collected 1.28 g of a yellow solid. Further heating yielded a further 2.48 g of the pure title product. $^1$H-NMR (ppm, CDCl3): 1.2 (d, 24H), 2.28 (s, 6H), 2.8 (m, 4H), 7.05–7.25 (m, 6H), 7.92 (t, 1H), 8.5 (d, 2H).

EXAMPLE 6

2,6-Diacetylpyridinebis(2-tert-butylphenylimine)

In a 200 mL round bottom flask, 2.0 g of 2,6-diacetylpyridine (FW 163.18, 0.0122 moles) was dissolved in 25 mL of methanol. Next 3.66 g of 2-tert-butylaniline (FW 149.24, 0.0245 moles) and 3 drops of formic acid were added. A precipitate started to form after 30 min. The solution was stirred at room temperature overnight. The precipitate was filtered off, washed with cold methanol and then dried. Collected 3.88 g (75% yield) of a yellow solid. The NMR revealed the solid to be mostly the monoimine product. The above solid (3.85 g, FW 294.4, 0.013 mole) was placed into a 200 mL flask. 1.95 g of 2-t-butylaniline, methanol, and 4 drops of formic acid were added. The mixture was brought to reflux before slowly adding chloroform until all solids had dissolved. After 48 h the volume was reduced and the reaction cooled to precipitate more solids. These were isolated and recrystallized from methanol and a minimum amount of chloroform, yielding 2.8 g of product. $^1$H-NMR (ppm, CDCl$_3$) 1.4 (s, 18H), 2.4 (s, 6H), 6.55 (d, 2H), 7.1 (t, 2H), 7.2 (t, 2H), 7.45 (d, 2H), 7.9 (t, 1H), 8.4 (d, 2H).

EXAMPLE 7

[2,6-Diacetylpyridinebis(2,6-diisopropylphenylimine)]cobalt[II]dichloride

In a dry, oxygen-free atmosphere CoCl$_2$ (anhydrous, 0.240 g) was dissolved in a minimum of dry THF. 2,6-Diacetylpyridinebis(2,6-diisopropylphenylimine) (0.893 g) was added and the solution turned dark and a brown precipitate formed. The mixture was stirred at room temperature for 3 days after which the solid product was filtered off, washed with pentane and dried. Yield 1.02 g. $^1$H-NMR (CD$_2$Cl$_2$) δ −84.1 (4, iPr-CH), −18.4 (12, iPr-CH$_3$), −17.0 (12, iPr-CH$_3$), −8.5 (2, Ar-H$_p$ or Py-H$_m$), 4.5 (6, N=C (CH$_3$)), 9.9 (4, Ar-H$_m$), 49.6 (1, Py-H$_p$), 116.5 (2, Ar-H$_p$ or Py-H$_m$).

Figure 2:
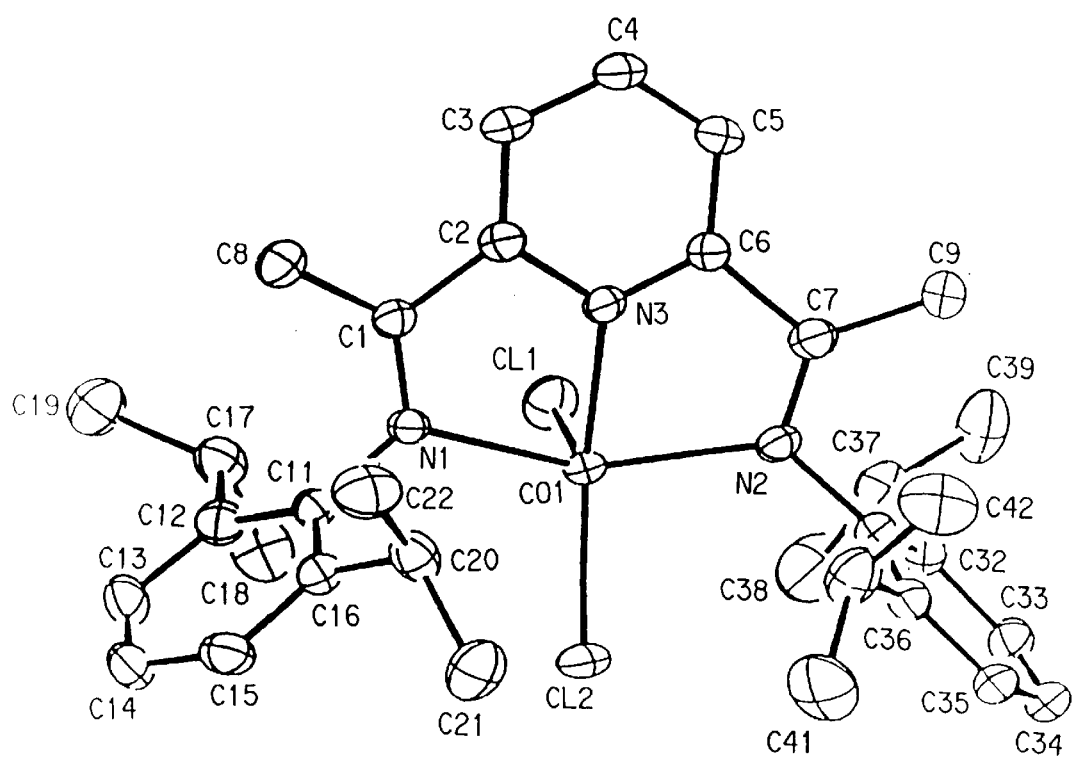
Figure 3:
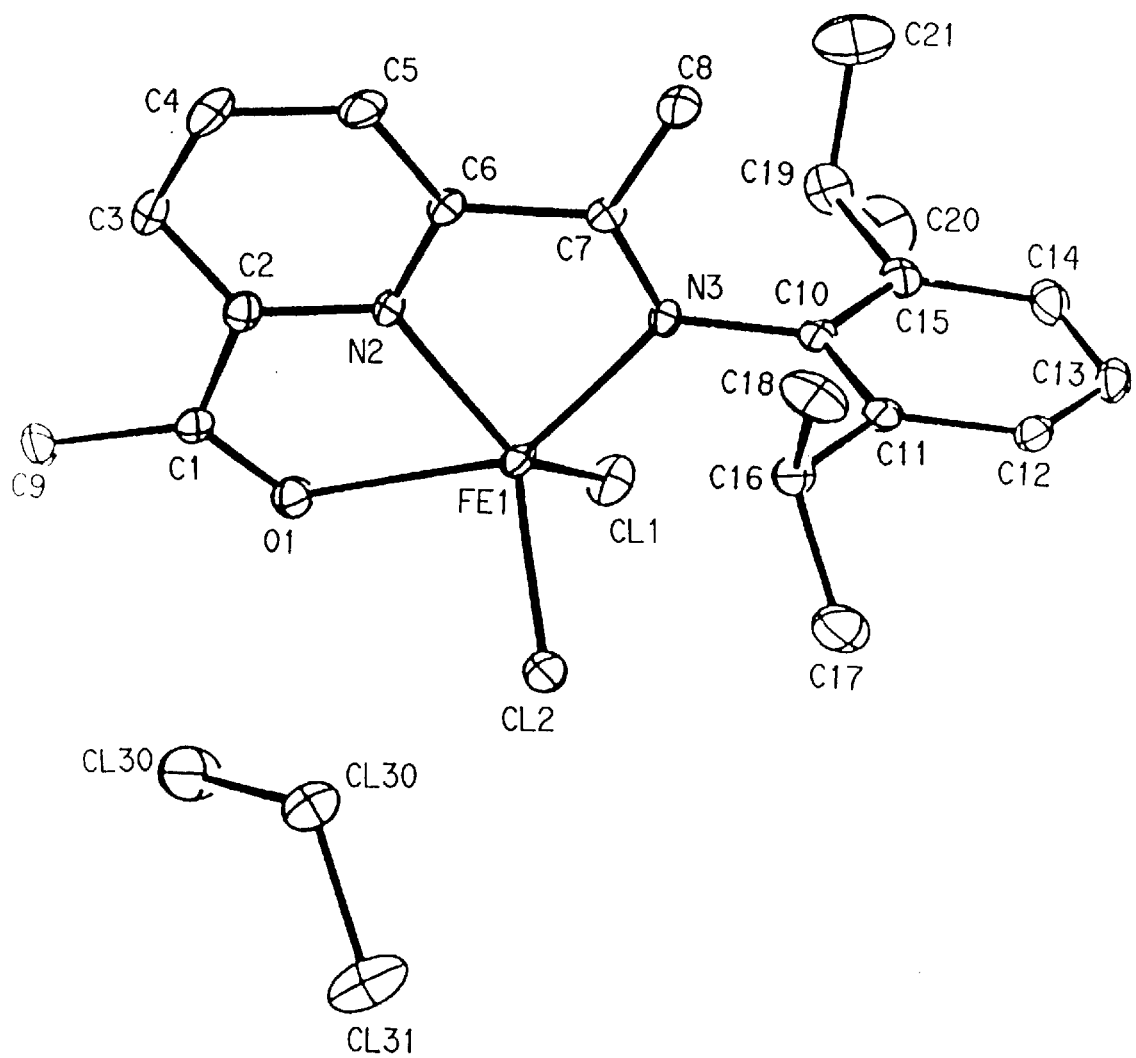

The structure of the cobalt complex was determined by X-ray crystallography. The compound is triclinic, P$_I$ (No. 2), a=9.786(1), b=20.741(1), c=8.673(1)Angstroms, α=91.69 (1), β=113.97(1), γ=83.62(1)°. Two views of this molecule are shown in FIGS. 1 and 2.

EXAMPLE 8

[2,6-Diacetylpyridinebis(2,6-diisopropylphenylimine)]iron[II]dichloride

In a dry, oxygen-free atmosphere FeCl$_2$ (anhydrous, 0.100 g) was slurried in 10 ml dry THF. 2,6-Diacetylpyridinebis (2,6-diisopropylphenylimine) (0.378 g) was added and the solution slowly turned dark and a blue precipitate formed. The mixture was stirred at room temperature for 3 days after which the product was filtered off, washed with pentane and dried. Yield 0.489 g. $^1$H-NMR (CD$_2$Cl$_2$) δ −36.3 (6, N=C (CH$_3$)), −21.5 (4, iPr-CH), −10.3 (2, Ar-H$_p$ or Py-H$_m$), −6.0 (12, iPr-CH$_3$), −5.1 (12, iPr-CH$_3$), 14.6 (4, Ar-H$_m$), 79.1 (1, Py-H$_p$), 79.5 (2, Ar-H$_p$ or Py-H$_m$).

The structure of the iron complex was determined by X-ray crystallography, and is similar to the cobalt complex made in Example 8. The compound is triclinic, P$_I$ (No. 2), a=9.789(2), b=20.740(5), c=8.714(1)Angstroms, α=91.72 (2), β=114.14(1), γ=83.25(1)°.

EXAMPLE 9

[2,6-Diacetylpyridinebis(2,6-diisopropylphenylimine)]iron[III]tribromide

In a dry, oxygen-free atmosphere FeBr$_3$ (anhydrous, 0.321 g) was slurried in 10 ml dry THF. 2,6-Diacetylpyridinebis(2,6-diisopropylphenylimine) (0.340 g) was added and the solution slowly turned dark orange brown. The mixture was stirred at RT for 3 d after which the volume was reduced and pentane added to precipitate the product, which was filtered off, washed with pentane and dried. Yield 0.620 g.

EXAMPLE 10

[2,6-Diacetylpyridinebis(2-chloro-6-methylphenylimine)]cobalt[II]dichloride

In a dry, oxygen-free atmosphere CoCl$_2$ (anhydrous, 0.062 g) was dissolved in a minimum of dry THF. 2,6-Diacetylpyridinebis(2-chloro-6-methylphenylimine) (0.205 g) was added and the solution turned green and a green precipitate formed. The mixture was stirred at RT for 2 days after which the volume of the solution was reduced by half and pentane added to precipitate the product, which was filtered off, washed with pentane and dried. Yield 0.240 g.

EXAMPLE 11

[2,6-Diacetylpyridinebis(2,4,6-trimethylphenylimine)]cobalt[II]dichloride

In a dry, oxygen-free atmosphere CoCl$_2$ (anhydrous, 0.140 g) was dissolved in a minimum of dry THF. 2,6-Diacetylpyridinebis(2,4,6-trimethylphenylimine) (0.460 g) was added and the solution turned green and a green precipitate formed. The mixture was stirred at room temperature for 4 d after which the product which was filtered off, washed with THF, and then pentane and dried. Yield 0.480 g.

EXAMPLE 12

[2,6-Diacetylpyridinebis(2-biphenylimine)]cobalt[II]dichloride

In a dry, oxygen-free atmosphere CoCl$_2$ (anhydrous, 0.135 g) was dissolved in a minimum of dry THF. 2,6-Diacetylpyridinebis(2-biphenylimine) (0.500 g) was added and the solution darkened and a brown precipitate formed. The mixture was stirred at RT for 2 d after which the volume was reduced and pentane added. The product was filtered off, washed with pentane and dried. Yield 0.500 g.

EXAMPLE 13

[2,6-Pyridinedicarboxaldehydebis(2,6-diisopropylphenylimine)]cobalt[II]dichloride In a dry, oxygen-free atmosphere CoCl$_2$ (anhydrous, 0.072 g) was dissolved in a minimum of dry THF. 2,6-Pyridinedicarboxaldehydebis(2,6-diisopropylphenylimine) (0.256 g) was added and the solution darkened and turned green. The mixture was stirred at RT for 4 d after which the volume was reduced and pentane added. The product was filtered off, washed with benzene and pentane and dried. Yield 0.26 g.

EXAMPLE 14

[2,6-Diacetylpyridinebis(2-t-butylphenylimine)]cobalt[II]dichloride

In a dry, oxygen-free atmosphere CoCl$_2$ (anhydrous, 0.168 g) was dissolved in a minimum of dry THF. 2,6-Diacetylpyridinebis(2-t-butylphenylimine) (0.553 g) was added and the solution darkened and a brown precipitate formed rapidly. The mixture was stirred at RT overnight after which pentane was added. The product was filtered off, washed with pentane and dried. Yield=0.66 g.

EXAMPLE 15

[2,6-Diacetylpyridinebis(2-t-butylphenylimine)]iron [II]dichloride

In a dry, oxygen-free atmosphere $FeCl_2$ (anhydrous, 0.085 g) was slurried in dry THF (10 ml). 2,6-Diacetylpyridinebis (2-tert-butylphenylimine) (0.285 g) was added and the solution darkened and a blue precipitate formed rapidly. The mixture was stirred at RT overnight after which pentane was added. The product was filtered off, washed with pentane and dried. Yield 0.30 g.

EXAMPLE 16

[2,6-Diacetylpyridinebis(2,6-diisopropylphenylimine)]cobalt[II]dibromide

In a dry, oxygen-free atmosphere $CoBr_2$ (anhydrous, 0.190 g) was slurried in dry THF (10 ml). 2,6-Diacetylpyridinebis(2,6-diisopropylphenylimine) (0.419 g) was added and the solution darkened to an olive green and a precipitate formed. The mixture was stirred at RT overnight after which the volume was reduced and pentane was added. The solid product was filtered off, washed with pentane and dried. Yield=0.65 g.

EXAMPLE 17

[[2,6-Diacetylpyridinebis(2,6-diisopropylphenylimine)]cobalt[II]bis(acetonitrile)] bis(tetrafluoroborate)

In a dry, oxygen-free atmosphere $CoCl_2$ (anhydrous, 0.848 g) was dissolved in 20 ml dry acetonitrile. $AgBF_4$ (2.543 g) was added and the solution stirred overnight. The solid AgCl was removed by filtration through Celite® and most of the acetonitrile was removed and diethyl ether added. The solution was shaken and the ether decanted. This was repeated several times until a solid product remained. Yield 2.8 g.

The cobalt salt prepared above (0.173 g) was dissolved in methylene chloride. 2,6-Diacetylpyridinebis(2,6-diisopropylphenylimine) (0.188 g) was added to give a clear red solution. This was stirred for 2 d at RT after which the solvent was removed and pentane added. The solid was filtered and washed 3 times with pentane and dried. Yield 0.271 g of a red/brown solid.

EXAMPLE 18

In a dry, oxygen-free atmosphere $Co(acac)_2$ (0.03 mmol) was dissolved in 25 ml dry toluene. 2,6-Diacetylpyridinebis (2,6-diisopropylphenylimine) (0.045 mmol) was added and the solution placed under 34.5 kPa of ethylene at room temperature. PMAO (0.7 ml) (9.5 wt % Al in toluene, Akzo) was added with vigorous stirring. The solution turned green and the temperature increased to ~60° C. Solid polymer rapidly precipitated. The reaction was allowed to run for 16 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 4.3 g polyethylene. Turnover #: 5109 mol $CH_2$=$CH_2$/mol Co. Mn=4294 (GPC, trichlorobenzene, 120° C., polyethylene standard). Tm (DSC)=131.85° C., ΔH=244.7 J/g.

EXAMPLE 19

In a dry, oxygen-free atmosphere the cobalt complex prepared in Example 17 (0.06 mmol) was dissolved in 25 ml dry toluene and the solution placed under 34.5 kPa of ethylene at room temperature. PMAO (0.8 ml) (9.5 wt % Al in toluene, Akzo) was added with vigorous stirring. The solution darkened and the temperature increased. Solid polymer rapidly precipitated. The mixture was stirred for 16 h at which time the reaction was terminated by addition of MeOH/10% HCl (15 ml). The polymer product was filtered, washed well with MeOH and acetone and dried. Yield 1.85 g polyethylene. Turnover #: 1099 mol $CH_2$=$CH_2$/mol Co. Mn=4364 (GPC, trichlorobenzene, 120° C., polyethylene standard), dispersity=3.0. Tm (DSC)=128.8° C., ΔH=246.4 J/g.

EXAMPLE 20

In a dry, oxygen-free atmosphere the cobalt complex prepared in Example 16 (0.06 mmol) was slurried in 25 ml dry toluene and the solution placed under 34.5 kPa of ethylene at room temperature. PMAO (0.8 ml) (9.5 wt % Al in toluene, Akzo) was added with vigorous stirring. The solution darkened and the temperature increased. Solid polymer rapidly precipitated. The reaction was allowed to run for 16 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 7.25 g polyethylene. Turnover #: 4307 mol $CH_2$=$CH_2$/mol Co. Mn=5094 (GPC, trichlorobenzene, 120° C., polyethylene standard), dispersity=4.0. Tm (DSC)=130.9° C., ΔH=226 J/g.

EXAMPLE 21

In a dry, oxygen-free atmosphere the cobalt complex prepared in Example 14 (0.03 mmol) was slurried in 25 ml dry toluene and the solution placed under 34.5 kPa of ethylene at room temperature. PMAO (0.8 ml) (9.5 wt % Al in toluene, Akzo) was added with vigorous stirring. The solution darkened and the temperature increased. Solid polymer rapidly precipitated. The reaction was allowed to run for 16 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 5.46 g polyethylene. Turnover #: 6487 mol $CH_2$=$CH_2$/mol Co. Mn=5031 (GPC, trichlorobenzene, 120° C., polyethylene standard), dispersity=6.2. Tm (DSC)=132.0° C., ΔH=252.7 J/g.

EXAMPLE 22

In a dry, oxygen-free atmosphere the iron(II) complex prepared in Example 15 (0.03 mmol) was slurried in 25 ml dry toluene and the solution placed under 34.5 kPa of ethylene at room temperature. PMAO (0.8 ml) (9.5 wt % Al in toluene, Akzo) was added with vigorous stirring. The solution darkened and the temperature increased. Solid polymer rapidly precipitated. The reaction was allowed to run for 17 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield=7.15 g polyethylene. Turnover #: 8495 mol $CH_2$=$CH_2$/mol Fe. Mn=2028 (GPC, trichlorobenzene, 120° C., polyethylene standard), dispersity=73. Tm (DSC)=131.3° C., ΔH=226.1 J/g.

EXAMPLE 23

In a dry, oxygen-free atmosphere the cobalt complex prepared in Example 7 (0.006 mmol) and 2,6-diacetylpyridinebis(2,6-diisopropylphenylimine) (0.006 mmol) were slurried in 50 ml dry toluene and the solution placed under 172 kPa of ethylene at room temperature in a Parr® autoclave. PMAO (0.6 ml) (9.5 wt % Al in toluene, Akzo) was added with vigorous stirring. The temperature increased to a maximum of 43° C. The reaction mixture was stirred for 1 h at constant pressure (172 kPa) after which time the reaction was terminated by addition of i-PrOH/10% HCl (15 ml). The polymer product was filtered, washed well with MeOH and acetone and dried. Yield=9.12 g polyethylene. Turnover #: 54181 mol $CH_2$=$CH_2$/mol Co. Mn=7725 (GPC, trichlorobenzene, 120° C., polyethylene standard), dispersity=4.1. Tm (DSC)=133.7° C., ΔH=251.6 J/g.

EXAMPLE 24

In a dry, oxygen-free atmosphere the iron(II) complex prepared in Example 15 (0.01 mmol) was slurried in 40 ml dry toluene and the solution placed under 138 kPa of ethylene at RT in a Parr® autoclave. PMAO (0.7 ml) (9.5 wt % Al in toluene, Akzo) was added with vigorous stirring. The temperature increased to a maximum of 56° C. The reaction mixture was stirred at constant pressure (131 kPa) for 19 min at which time the reaction was terminated by addition of i-PrOH/10% HCl (15 ml). The polymer product was filtered, washed well with MeOH and acetone and dried. Yield 7.88 g polyethylene. Turnover #: 28088 mol $CH_2$=$CH_2$/mol Fe. Mn=3076 (GPC, trichlorobenzene, 120° C., polyethylene standard), dispersity=31. Tm (DSC)= 132.2° C., ΔH=233.9 J/g.

EXAMPLE 25

In a dry, oxygen-free atmosphere the cobalt complex prepared in Example 7 (0.007 mmol) was slurried in 50 ml dry toluene and the solution placed under 172 kPa of ethylene at RT in a Parr® autoclave. PMAO (0.6 ml) (9.5 wt % Al in toluene, Akzo) was added with vigorous stirring. The temperature increased to a maximum of 43° C. The reaction mixture was stirred for 2 h at constant pressure (172 kPa) after which time the reaction was terminated by addition of i-PrOH/10% HCl (15 ml). The polymer product was filtered, washed well with MeOH and acetone and dried. Yield 11.1 g polyethylene. Turnover #: 56523 mol $CH_2$=$CH_2$/mol Co. Mn=7840 (GPC, trichlorobenzene, 120° C., polyethylene standard), dispersity=3.0. Tm (DSC)= 132.7° C., ΔH=251.9 J/g.

EXAMPLE 26

In a dry, oxygen-free atmosphere the cobalt complex prepared in Example 7 (0.016 mmol) was slurried in 50 ml dry toluene and the solution placed under 689 kPa of ethylene at RT in a Parr® autoclave. PMAO (0.4 ml) (9.5 wt % Al in toluene, Akzo) was added with vigorous stirring. The temperature increased to a maximum of 75° C. in 6 min at which time the reaction was terminated by addition of i-PrOH/10% HCl (15 ml). The polymer product was filtered, washed well with MeOH and acetone and dried. Yield 11.1 g polyethylene. Turnover #: 18963 mol $CH_2$=$CH_2$/mol Co. Mn=4733 (GPC, trichlorobenzene, 120° C., polyethylene standard), dispersity=2.85. Tm (DSC)=131.4° C., ΔH=244.7 J/g.

EXAMPLE 27

In a dry, oxygen-free atmosphere the cobalt complex prepared in Example 7 (0.06 mmol) was slurried in 25 ml dry toluene and the solution placed under 34.5 kPa of ethylene at RT. PMAO (0.6 ml) (9.5 wt % Al in toluene, Akzo) was added with vigorous stirring. The solution darkened and the temperature increased. Solid polymer rapidly precipitated. The reaction was allowed to run for 17 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 5.21 g polyethylene. Turnover #: 3095 mol $CH_2$=$CH_2$/mol Co. Mn=10014 (GPC, trichlorobenzene, 120° C., polyethylene standard), dispersity=4.6. Density (gradient tube) 0.974±0.01%. Methyl and olefin ends (no branches) are visible in the $^{13}$C-NMR spectrum (trichlorobenzene, 120° C.).

EXAMPLE 28

In a dry, oxygen-free atmosphere the iron(III) complex prepared in Example 9 (0.06 mmol) was slurried in 25 ml dry toluene and the solution placed under 34.5 kPa of ethylene at room temperature. PMAO (0.6 ml) (9.5 wt % Al in toluene, Akzo) was added with vigorous stirring. The solution darkened and the temperature increased. Solid polymer rapidly precipitated. The mixture was stirred for 17 h at which time the reaction was terminated by addition of MeOH/10% HCl (15 ml). The polymer product was filtered, washed well with MeOH and acetone and dried. Yield 2.0 g polyethylene. Turnover #: 1188 mol $CH_2$=$CH_2$/mol Fe. Mn=2699 (GPC, trichlorobenzene, 120° C., polyethylene standard), dispersity=134.

EXAMPLE 29

In a dry, oxygen-free atmosphere the iron(II) complex prepared in Example 8 (0.056 mmol) was slurried in 25 ml dry toluene and the solution placed under 34.5 kPa of ethylene at RT. PMAO (0.7 ml) (9.5 wt % Al in toluene, Akzo) was added with vigorous stirring. The solution turned orange and then darkened and after a short initiation time the temperature increased. Solid polymer rapidly precipitated. The reaction was allowed to run for 16 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 4.56 g polyethylene. Turnover #: 2902 mol $CH_2$=$CH_2$/mol Fe. Mn=1820 (GPC, trichlorobenzene, 120° C., polyethylene standard), dispersity=98. Tm (DSC)= 130.6° C., ΔH=229.0 J/g.

EXAMPLE 30

In a dry, oxygen-free atmosphere the cobalt complex prepared in Example 10 (0.015 mmol) was slurried in 25 ml dry toluene and the solution placed under 34.5 kPa of ethylene at 0° C. PMAO (0.4 ml) (9.5 wt % Al in toluene, Akzo) was added with vigorous stirring. The solution darkened and the temperature increased. Solid polymer rapidly precipitated. The reaction was allowed to run for 17 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 3.26 g polyethylene. Turnover #: 7746 mol $CH_2=CH_2$/mol Co. Mn=420 (GPC, trichlorobenzene, 120° C., polyethylene standard), dispersity=2.1.

EXAMPLE 31

In a dry, oxygen-free atmosphere the cobalt complex prepared in Example 11 (0.06 mmol) was slurried in 25 ml dry toluene and the solution placed under 34.5 kPa of ethylene at RT. PMAO (0.8 ml) (9.5 wt % Al in toluene, Akzo) was added with vigorous stirring. The solution darkened and the temperature increased. Solid polymer rapidly precipitated. The reaction was allowed to run for 17 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 6.6 g polyethylene. Turnover #: 3921 mol $CH_2=CH_2$/mol Co. Mn=697 (GPC, trichlorobenzene, 120° C., polyethylene standard), dispersity=2.5.

EXAMPLE 32

In a dry, oxygen-free atmosphere the cobalt complex prepared in Example 12 (0.05 mmol) was slurried in 25 ml dry toluene and the solution placed under 34.5 kPa of ethylene at room temperature. PMAO (0.8 ml) (9.5 wt % Al in toluene, Akzo) was added with vigorous stirring. The solution darkened and the temperature increased. Solid polymer rapidly precipitated. The mixture was stirred for 17 h at which time the reaction was terminated by addition of MeOH/10% HCl (15 ml). Yield ~10 g oligomer product. Turnover #: 7129 mol $CH_2=CH_2$/mol Co. Oligomers are linear with decene as the major product. Oligomers are mainly linear internal olefins. Using $^{13}$C-NMR (CDCl$_3$) and GC-MS the distribution of oligomers with 10 or more C atoms was found to be the following: 3-methylene olefin (1.2%), 4+ methylene olefin (0.8%), alpha-olefin (9.0%), trans-2-olefin (16.0%), cis-2-olefin (5.6%), trans-3-olefin (30.2%), cis-3-olefin (6.5%), trans-4-olefin (21.1%), remainder of olefins (9.3%). Based on gas chromatography analysis, the approximate weight distribution of the oligomers is: $C_{10}$—63%; $C_{12}$—25%; $C_{14}$—9%; $C_{16}$—3%. Based on the gas chromatography of the crude reaction mixture there was also a significant amount of $C_8$ compounds present in the original product mix.

EXAMPLE 33

In a dry, oxygen-free atmosphere the cobalt complex prepared in Example 13 (0.06 mmol) was slurried in 25 ml dry toluene and the solution placed under 34.5 kPa of ethylene at RT. PMAO (0.8 ml) (9.5 wt % Al in toluene, Akzo) was added with vigorous stirring. The solution darkened and the reaction was allowed to run for 17 h at which time the surface of the mixture had formed a solid polymer crust thus preventing further polymerization. The reaction was terminated by addition of MeOH/10% HCl (15 ml). The polymer product was filtered, washed well with MeOH and acetone and dried. Yield 3.6 g polyethylene. Turnover #: 2138 mol $CH_2=CH_2$/mol Co. Mn=766 (GPC, trichlorobenzene, 120° C., polyethylene standard), dispersity=2.4.

EXAMPLE 34

In a dry, oxygen-free atmosphere the iron(II) complex prepared in Example 8 (0.01 mmol) was slurried in 70 ml toluene, cooled to −12° C. and placed under 34.5 kPa of ethylene. PMAO (0.8 ml) (9.5 wt % Al in toluene, Akzo) was added with vigorous stirring. After several minutes solid polymer was visible and stirring became erratic. The reaction was terminated after 120 minutes by addition of MeOH/10% HCl (20 ml). The polymer product was filtered, washed well with MeOH and acetone and dried. Yield=5.1 g. Turnover #: 16832 mol $CH_2=CH_2$/mol Fe. No branching could be detected from the $^1$H-NMR. Mn=433007 (GPC, trichlorobenzene, 120° C., polyethylene standards), dispersity=2.9. Tm (DSC)=134.0° C. ΔH=197.1 J/g.

EXAMPLE 35

2,6-diacetyl-4-trifluoromethylpyridinebis[(2,6-diisopropyl)phenylimine]

In a 20 ml vial, 0.247 g 2,6-diacetyl-4-trifluoromethyl-pyridine (FW. 232.19, 0.00106 mole) and 5 mL of methanol were placed. Next 0.440 g of 2,6-diisopropylaniline (FW. 177.29, 0.00248 mol) was added. This reaction solution was stirred overnight. A precipitate formed and was filtered off, washed with methanol and dried under vacuum. Collected 0.17 g. The filtrate was place back inside the original vial and stirred for 1 more day. More precipitate formed and was filtered off, washed and dried. Collected another 0.16 g. $^1$H-NMR (ppm, CDCl$_3$): 1.2 (multiplet, 24H), 2.85 (multiplet, 4H), 7.1–7.25 (multiplet, 6H), 8.7 (singlet, 2H).

EXAMPLE 36

[2,6-diacetyl-4-trifluoromethylpyridinebis{(2,6-diisopropyl)phenylimine}]cobalt(II)chloride In a dry, oxygen-free atmosphere, CoCl$_2$ (anhydrous, 0.040 g) was dissolved in dry THF. 2,6-Diacetyl-4-trifluoromethylpyridinebis[(2,6-disopropyl)phenylimine] (0.170 g) was added and the solution turned brown/red. After stirring for 3 days the volume of the solution was reduced and pentane added. The solid product was filtered off, washed with pentane and dried. Yield=0.166 g.

EXAMPLE 37

In a dry, oxygen-free atmosphere the cobalt(II) complex prepared in Example 36 (0.03 mmol) was dissolved in 25 ml toluene and placed under 34.5 kPa of ethylene at room temperature. PMAO (0.8 ml) (9.5 wt % Al in toluene, Akzo) was added with vigorous stirring. The reaction mixture turned blue/black and the temperature increased. The reaction was terminated after 16 h by addition of MeOH/10% HCl (15 ml). The polymer product was filtered, washed well with MeOH and acetone and dried. Yield=4.8 g. Turnover #: 5703 mol $CH_2=CH_2$/mol Co. Mn=17950 (GPC, trichlorobenzene, 120° C., polyethylene standard), dispersity=16.5. Tm (DSC)=133.1° C. ΔH=226.0 J/g.

EXAMPLE 38

N,N'-bis[(2,6-diisopropyl)phenyl]pyridine-2,6-dicarboxamide

Inside the dry box under nitrogen, 10.0 g of 2,6-pyridinebis(carbonyl chloride) (FW. 204, 0.049 mole, Aldrich Chemical Co., 97%) and 75 mL of dry THF were placed inside a 300 mL round bottom flask along with a large magnetic stir bar. The flask was sealed under nitrogen and brought outside the dry box and then attached to a nitrogen bubbler. Then 12.4 g of triethylamine (FW. 101.21, 0.1225 mole) was added quickly. While stirring vigorously, 17.38 g of 2,6-diisopropylaniline (FW. 177.29, 0.098 mole) was added via a dropping funnel. During the addition a large exotherm occurred and a white precipitate immediately formed. The resulting mixture was stirred for 3 hours, then filtered through a frit to remove the $NEt_3.HCl$, the precipitate. The filtrate was passed quickly through a frit containing silica gel which was washed well with warm THF. The filtrate was reduced in volume and placed inside the refrigerator for crystallization. The precipitate was isolated and dried under vacuum. Collected 15.17 g of a white solid. The remaining liquid was concentrated and cooled but no solids formed. The solvent was then removed and the remaining residue was taken up in a minimum amount of methanol with a large excess of hexane and placed in the refrigerator for recrystallization. Collected 13.91 g of a white solid. A $^1H$ NMR revealed these products to be pure with one THF molecule cocrystallizing. $^1$H-NMR (ppm, $CDCl_3$): 1.22 (doublet, 24H), 3.15 (multiplet, 4H), 7.25 (doublet, 4H), 7.35 (triplet, 2H), 8.2 (triplet, 1H), 8.55 (doublet, 2H), 9.0 (singlet, broad, 2H).

EXAMPLE 39

N,N'-bis[(2,6-diisopropyl)phenyl]pyridine-2,6-bis (iminochloride)

Inside the dry box under nitrogen, 13.91 g of the product from Example 38 (FW. 485.7, 0.0286 moles) was placed inside a 500 mL round bottom three neck flask. Next 300 mL of dry toluene was added followed by 12.2 g of $PCl_5$ (FW. 203.22, 0.0601 mole). The flask was sealed under nitrogen and brought outside the dry box where a condenser and nitrogen bubbler was attached to one neck of the flask and an adapter going to a KOH solution was attached to another neck of the flask. Nitrogen was slowly passed in through the condenser and out through the adapter and bubbled through the KOH solution. The reaction was then heated to 80° C. for two hours during which HCl evolved from the reaction and was neutralized in the basic solution. Next the reaction was stripped of solvent and the remaining solid was recrystallized from THF. Collected 4.39 g of a yellow solid. $^1$H-NMR confirmed this to be pure product. $^1$H-NMR (ppm, $CDCl_3$): 1.2 (multiplet, broad, 24H), 2.85 (multiplet, 4H), 7.22 (singlet, 6H), 8.1 (triplet, 1H), 8.55 (doublet, 2H).

EXAMPLE 40

S,S'-Dimethyl Pyridine-2,6-bis[N,N'(2,6-diisopropylphenyl)carboximidothioate]

In a dry, oxygen-free atmosphere the compound prepared in Example 39 (0.427 g) was placed in THF (10 ml) and NaSMe (0.228 g) was added. The mixture was heated at 60° C. for 3 days at which time the solids were removed by filtration and the filtrate evaporated to dryness. Toluene was added and the solution filtered and evaporated to dryness. The $^1$H NMR spectrum indicated that the reaction was complete. $^1$H NMR (ppm, THF-$d_8$): 1.05 (doublet, 12H), 1.1 (doublet, 12H), 2.3 (singlet, 6H), 2.9 (multiplet, 4H), 7.0 (triplet, 2H), 7.1 (doublet, 4H), 7.6 and 7.8 (broad, 3H).

EXAMPLE 41

S,S'-Dimethyl pyridine-2,6-bis[N,N'(2,6-disopropylphenyl)carboximidothioate]cobalt(II) chloride In a dry, oxygen-free atmosphere, $CoCl_2$ (anhydrous, 0.060 g) was dissolved in dry THF. S,S'-Dimethyl pyridine-2,6-bis[N,N'-(2,6-disopropylphenyl)carboximidothioate] (0.253 g, 2 eq) was added and the solution turned green. After stirring for 3 days a brown solid had precipitated from solution. The volume of the solution was reduced and pentane added. The solid product was filtered off, washed with pentane and dried. Yield=0.252 g.

EXAMPLE 42

In a dry, oxygen-free atmosphere the cobalt[II] complex prepared in Example 41 (0.03 mmol) was slurried in 25 ml toluene and placed under 34.5 kPa of ethylene at room temperature. PMAO (0.8 ml) (9.5 wt % Al in toluene, Akzo) was added with vigorous stirring. The reaction mixture turned blue/green and the temperature increased. The reaction was terminated after 16 hr. by addition of MeOH/10% HCl (15 ml). The polymer product was filtered, washed well with MeOH and acetone and dried. Yield=2.33 g. Turnover #: 2768 mol $CH_2=CH_2$/mol Co.

EXAMPLE 43

Inside a dry box under nitrogen, 36.0 mg of the cobalt compound prepared in Example 7 was weighed into a vial and toluene (15 ml) was added. The solution was shaken until the catalyst was partly dissolved. Silica supported MAO (0.5 g, 14.3 wt. % Al, Grace Davison) was added to the vial and the solution shaken for 20 min. The solids were filtered, washed with toluene until the washings were colorless and then washed twice with pentane. The product was dried under vacuum and stored inside a drybox freezer. Collected 0.473 g of solid. It contained 13.0% Al and 0.52% Co.

The above solid (160 mg) was slurried in 5 mL of cyclohexane and transferred into a disposable 5 mL syringe. The slurry was removed from the drybox and added to 150 mL of dry, degassed 2,2,4-trimethylpentane in a 600 ml Parr® reactor under nitrogen. The reactor was sealed, stirring started and then heated to 35° C. and pressurized with ethylene to 1.0 MPa. After 30 min the pressure was released and the reaction quenched with MeOH. The polymer was removed, filtered, washed with methanol then acetone, and dried. Collected 2.55 g of polyethylene. Tm (DSC, 10° C./min, $N_2$)=134.8° C., $\Delta H$=182.7 J/g. Turnover #=8263.

EXAMPLE 44

Inside a dry box under nitrogen, 36.0 mg of the iron compound prepared in Example 8 was weighed into a vial and toluene (15 ml) was added. The solution was shaken until the catalyst was partly dissolved. Silica supported MAO (0.5 g, 14.3 wt. % Al, Grace Davison) was added to the vial and the solution shaken for 20 min. The solids were filtered, washed with toluene until the washings were colorless and then washed twice with pentane. The product was dried under vacuum and stored inside the drybox freezer. Collected 0.502 g of solid. It contained 13.5% Al and 0.40% Fe.

The above solid (160 mg) was slurried in 5 mL of cyclohexane and transferred into a disposable 5 mL syringe. The slurry was removed from the drybox and added to 150 mL of dry, degassed 2,2,4-trimethylpentane in a 600 ml Parr® reactor under nitrogen. The reactor was sealed, stirring started and then heated to 35° C. and pressurized with ethylene to 1.0 MPa. After 30 min the pressure was released and the reaction quenched with MeOH. The polymer was removed, filtered, washed with methanol then acetone, and dried. Collected 1.1 g of polyethylene. Tm (DSC, 10° C./min, $N_2$)=135.6° C. Turnover #=2800.

EXAMPLE 45

Inside a dry box under nitrogen, 36.0 mg of the cobalt compound prepared in Example 7 was weighed into a vial and toluene (15 ml) was added. The solution was shaken until the catalyst was partly dissolved. Dry cyclopentene (10 eq, 0.046 ml) was added followed by silica supported MAO (0.5 g, 14.3 wt. % Al, Grace Davison) and the solution shaken for 10 min. The solids were filtered, washed with toluene until the washings were colorless and then washed twice with pentane. The product was dried under vacuum and stored inside a drybox freezer. Collected 0.472 g of purple solid. It contained 14.5% Al and 0.7% Co.

The above solid (160 mg) was slurried in 4 mL of cyclohexane and transferred into a disposable 5 mL syringe. The slurry was removed from the drybox and added to 150 mL of dry, degassed 2,2,4-trimethylpentane in a 600 ml Parr® reactor under nitrogen. The reactor was sealed, stirring started and then heated to 35° C. and pressurized with ethylene to 1.0 MPa. After 30 min the pressure was released and the reaction quenched with MeOH. The polymer was removed, filtered, washed with methanol then acetone, and dried. Collected 1.5 g of polyethylene. Tm (DSC, 10° C./min, $N_2$)=135.6° C., $\Delta H$=184.0 J/g. Turnover #=2814.

EXAMPLE 46

Inside a dry box under nitrogen, 36.0 mg of the cobalt compound prepared in Example 7 was weighed into a vial and toluene (15 ml) was added. The solution was shaken until the catalyst was partly dissolved. Next 0.6 ml PMAO-IP (Akzo, 12.9% Al in toluene, an "improved" grade of PMAO whose solution is clear) was added and the solution shaken for 1 min. Dehydrated silica (0.5 g, XPO-2402, Grace Davison) was added to the vial and the solution shaken for a further 10 min. The solids were filtered, washed with toluene until the washings were colorless and then washed twice with pentane. The product was dried under vacuum and stored inside a drybox freezer. Collected 0.660 g of solid. It contained 9.16% Al and 0.36% Co.

The above solid (160 mg) was slurried in 4 mL of cyclohexane and transferred into a disposable 5 mL syringe. The slurry was removed from the drybox and added to 150 mL of dry, degassed 2,2,4-trimethylpentane in a 600 ml Parr® reactor under nitrogen. The reactor was sealed, stirring started and then heated to 35° C. and pressurized with ethylene to 1.0 MPa. After 30 min the pressure was released and the reaction quenched with MeOH. The polymer was removed, filtered, washed with methanol then acetone, and dried. Collected 2.06 g of polyethylene. Tm (DSC, 10° C./min, $N_2$)=137.4° C., $\Delta H$=184.0 J/g. Turnover #=7516.

EXAMPLE 47

The cobalt complex prepared in Example 7 (3.3 mg) was weighed into a vial and dissolved in dry dichloromethane (5 ml). PMAO (4.4 ml, Akzo 9.5 wt % Al) was placed in 500 ml dry toluene and placed in a 1 L stirred autoclave under nitrogen at room temperature. The cobalt complex was added and at the same time the reactor was pressurized to 43 MPa with ethylene. The reaction was allowed to run for 2 min at which time cold water was admitted to internal cooling coils to control internal temperature. After 4 min the temperature had reached 38.7° C. The reaction was quenched by addition of MeOH/10% HCl solution and the polymer filtered from solution, washed with MeOH and finally acetone and dried. Yield=60.4 g. Mn (GPC, trichlorobenzene, 120° C., polyethylene standard)=8913, dispersity=2.4. Tm (DSC)=133.3° C. $\Delta H$=226.8 J/g. Turnover #=445,508.

EXAMPLE 48

The iron complex prepared in Example 8 (2.0 mg) was weighed into a vial and dissolved in dry dichloromethane (5 ml). PMAO (3.4 ml, Akzo 9.5wt % Al) was placed in 500 ml dry toluene and placed in a 1 L stirred autoclave under nitrogen at room temperature. The cobalt complex was added and at the same time the reactor was pressurized to 39 MPa with ethylene. The reaction was allowed to run for 2 min with water cooling after which time the temperature had increased to 94° C. The reaction was quenched by addition of MeOH/10% HCl solution and the polymer filtered from solution, washed with MeOH and finally acetone and dried. Yield=64.5 g. Mn (GPC, trichlorobenzene, 120° C., polyethylene standard)=11979, dispersity=3.7. Tm (DSC)=133.1° C. $\Delta H$=225.3 J/g. Turnover #=781,539.

EXAMPLE 49

In a dry, oxygen-free atmosphere the cobalt[II] complex prepared in Example 7 (0.03 mmol) was dissolved in 25 ml toluene and placed under 34.5 kPa of ethylene at room temperature. $Et_2AlCl$ (0.75 ml, 2M in hexane, Aldrich) was added with vigorous stirring. The reaction mixture turned green and finally blue/black and the temperature increased. The reaction was terminated after 16 hr by addition of MeOH/10% HCl (15 ml). The polymer product was filtered, washed well with MeOH and acetone and dried. Yield=1.5 g. Turnover #: 1782 mol $CH_2=CH_2$/mol Co. Mn=4350 (GPC, trichlorobenzene, 120° C., polyethylene standards), dispersity=17.6.

EXAMPLE 50

In a dry, oxygen-free atmosphere the iron[II] complex prepared in Example 8 (0.0028 mmol) was slurried in 80 ml toluene, cooled to −12° C. and placed under 34.5 kPa of ethylene. PMAO (1.0 ml) (9.5 wt % Al in toluene, Akzo) was added with vigorous stirring. After several min solid polymer was visible and stirring became erratic. The reaction was terminated after 180 min at which time stirring had stopped. It was quenched by addition of MeOH/10% HCl (20 ml). The polymer product was filtered, washed well with MeOH and acetone and dried. Yield=6.61 g. Turnover #: 84130 mol $CH_2=CH_2$/mol Fe. No branching could be detected from the $^1$H-NMR. Methyl end groups (no branches) are detected in $^{13}$C-NMR analysis. No olefin ends are visible. This indicates that the low Mn fraction present probably arises due to chain transfer to Al. Mn=7458 (GPC, trichlorobenzene, 120° C., polyethylene standards), dispersity=73. Tm (DSC)=133.6° C. $\Delta H$=224.0 J/g.

EXAMPLE 51

[2,6-diacetyl-4-trifluoromethylpyridinebis{(2,6-diisopropyl)phenylimine}]iron[II]chloride In a dry, oxygen-free atmosphere, $FeCl_2$ (anhydrous, 0.020 g) was dissolved in dry THF. 2,6-Diacetyl-4-trifluoromethylpyridinebis[(2,6-diisopropyl)phenylimine] (0.096 g) was added and the solution turned dark blue/green. After stirring for 3 days the solvent was removed and the solids taken up in dry $CH_2Cl_2$. The solution was filtered and the volume reduced and pentane added. The solid product was filtered off, washed with pentane and dried. Yield=0.085 g.

EXAMPLE 52

In a dry, oxygen-free atmosphere the cobalt(II) complex prepared in Example 36 (0.0028 mmol) was slurried in 50 ml dry toluene and the solution placed under 700 kPa of ethylene at 45° C. in a 100 ml stirred Parr® autoclave. PMAO-IP (0.5 ml) (12.8 wt % Al in toluene, Akzo) was added with vigorous stirring. The temperature increased to 55° C. The reaction mixture was stirred for 10 min at constant pressure (700 kPa) after which time the reaction was terminated by addition of MeOH/10% HCl (10 ml). The polymer product was filtered, washed well with MeOH and acetone and dried. Yield=4.2 g polyethylene. Turnover #: 53456 mol $CH_2=CH_2$/mol Co.

EXAMPLE 53

In a dry, oxygen-free atmosphere the iron[II] complex prepared in Example 51 (0.0015 mmol) was slurried in 50 ml dry toluene and the solution placed under 700 kPa of ethylene 45° C. in a 100 ml stirred Parr® autoclave. PMAO-IP (0.5 ml) (12.8 wt % Al in toluene, Akzo) was added with vigorous stirring. The temperature increased to 60° C. The reaction mixture was stirred for 10 min at constant pressure (670 kPa) after which time the reaction was terminated by addition of MeOH/10% HCl (10 ml). The polymer product was filtered, washed well with MeOH and acetone and dried. Yield=5.0 g polyethylene. Turnover #: 118793 mol $CH_2=CH_2$/mol Fe.

EXAMPLE 54

In a dry, oxygen-free atmosphere the cobalt[II] complex prepared in Example 7 (0.008 mmol) was slurried in 50 ml toluene, cooled to −12° C. and placed under 34.5 kPa of ethylene. PMAO (0.2 ml) (9.5 wt % Al in toluene, Akzo) was added with vigorous stirring. After several min solid polymer was visible. The reaction was terminated after 23 min at which time stirring had stopped. It was quenched by addition of MeOH/10% HCl (10 ml). The polymer product was filtered, washed well with MeOH and acetone and dried. Yield=2.46 g. Turnover #: 10959 mol $CH_2=CH_2$/mol Co. Mn=41600 (GPC, trichlorobenzene, 120° C., polyethylene standards), dispersity=2.26. Tm (DSC)=132.9° C. ΔH=196.2 J/g.

EXAMPLE 55

The cobalt[II] complex prepared in example 7 (0.07 mmol) was dissolved in dichloroethane and $SiO_2$ (dehydrated at 500° C. under $N_2$) was added. The solution was stirred for 2 h after which the solids were filtered, washed well with DCE and dried. The product was a yellow powder. ICP analysis: % Co=0.32%, % Si=41.8%.

The supported cobalt complex prepared above (85 mg, 0.0046 mmol) was slurried in dry pentane and placed under 34.5 kPa of ethylene. PMAO (0.6 ml, 9.5 wt % Al in toluene, Akzo) was added with stirring. The temperature of the reaction mixture increased. After 16 h the reaction was quenched by addition of MeOH/10% HCl (10 ml) and the polymer product filtered, washed well with MeOH and finally acetone and dried. Yield=1.8 g. Turnover #=13945 mol $CH_2=CH_2$/mol Co. Tm (DSC)=131.7° C. ΔH=178.6 J/g.

EXAMPLE 56

The cobalt[II] complex prepared in example 7 (0.07 mmol) was dissolved in dichloroethane and $SiO_2$ (dehydrated at 500° C. under $N_2$) was added. The solution was stirred for 2 h after which the solvent was slowly removed under vacuum and the solids dried. The product was a yellow/green powder. ICP analysis: % Co=0.33%, % Si=37.3%.

The supported cobalt complex prepared above (100 mg, 0.0056 mmol) was slurried in dry pentane (10 ml) and placed under 34.5 kPa of ethylene. PMAO (0.6 ml, 9.5 wt % Al in toluene, Akzo) was added with stirring. The temperature of the reaction mixture increased. After 16 h the reaction was quenched by addition of MeOH/10% HCl (10 ml) and the polymer product filtered, washed well with MeOH and finally acetone and dried. Yield=1.62 g. Turnover #=10310 mol $CH_2=CH_2$/mol Co. Tm (DSC)=136.8° C. ΔH=193.1 J/g.

EXAMPLE 57

In a dry, oxygen-free atmosphere the compound prepared in Example 39 (0.322 g) was placed in THF (10 ml) and the sodium derivative of imidazole (0.300 g) was added. The mixture was heated at 60° C. for 10 days at which time the solids were removed by filtration and the filtrate evaporated to dryness. Pentane was added to the oily solid and the solution stood overnight after which time the oil had solidified. The product was filtered, washed with pentane and dried, to give

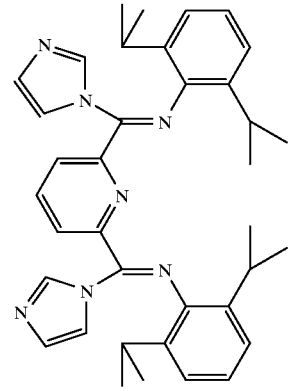

(XIII)

EXAMPLE 58

In a dry, oxygen-free atmosphere $FeCl_2$ (anhydrous, 0.015 g) was dissolved in dry THF. The ligand prepared in example 59 (0.060 g) was added and the solution turned yellow. After stirring for 3 days a brown solid had precipitated from solution. After 7 days the volume of the solution was reduced and pentane added. The solid product was filtered off, washed with pentane and dried. Yield=0.046 g beige solid of the formula

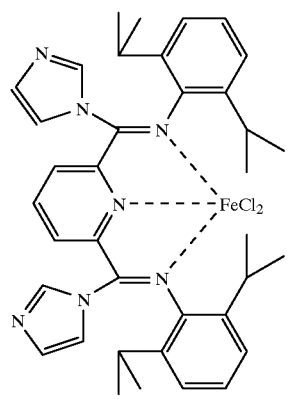

(XIV)

EXAMPLE 59

In a dry, oxygen-free atmosphere the iron[II] complex prepared in Example 58 (0.03 mmol) was slurried in 25 ml toluene and placed under 34.5 kPa of ethylene at room temperature. PMAO (0.6 ml) (9.5 wt % Al in toluene, Akzo) was added with vigorous stirring. The reaction mixture turned red/brown and the temperature increased. The reaction was terminated after 16 h (after which time the a solid crust of polymer had formed over the top of the flask) by addition of MeOH/10% HCl (15 ml). The polymer product was filtered, washed well with MeOH and acetone and dried. Yield=2.51 g. Turnover #: 2982 mol $CH_2=CH_2$/mol Fe. Tm (DSC)=131.5° C. ΔH=190.9 J/g.

EXAMPLE 60

In a dry, oxygen-free atmosphere the cobalt[II] complex prepared in Example 7 (0.03 mmol) was dissolved in 25 ml toluene and placed under 34.5 kPa of ethylene at room temperature. $B(C_6F_5)_3$ (0.09 mmol in toluene) was added with vigorous stirring. No visible change occurred. Next $AlEt_3$ (0.09 mmol in 3 ml toluene) was added. The solution turned dark green then blue/black and the temperature increased. The reaction was terminated after 16 h by addition of MeOH/10% HCl (15 ml). The polymer product was filtered, washed well with MeOH and acetone and dried. Yield=3.9 g. Turnover #: 4670 mol $CH_2=CH_2$/mol Co. Mn=7233 (GPC, trichlorobenzene, 120° C., polyethylene standards), dispersity=3.3. Tm (DSC)=135.3° C. ΔH=240.5 J/g.

EXAMPLE 61

In a dry, oxygen-free atmosphere the cobalt[II] complex prepared in Example 7 (0.03 mmol) was dissolved in 25 ml toluene and placed under 34.5 kPa of ethylene at room temperature. $AlEt_3$ (0.23 mmol in toluene) was added with vigorous stirring. The mixture changed to a deep purple solution. Next, $B(C_6F_5)_3$ (0.09 mmol in toluene) was added. The solution turned dark blue. The reaction was terminated after 16 hrs by addition of MeOH/10% HCl (15 ml). The polymer product was filtered, washed well with MeOH and acetone and dried. Yield=6.4 g. Turnover #: 7557 mol $CH_2=CH_2$/mol Co. Mn=6777 (GPC, trichlorobenzene, 120° C., polyethylene standards), dispersity=3.4. Tm (DSC)=134.3° C. ΔH=235.3 J/g.

What is claimed is:

1. A process for the polymerization of ethylene, comprising, contacting, at a temperature of about −100° C. to about +200° C., a compound of the formula

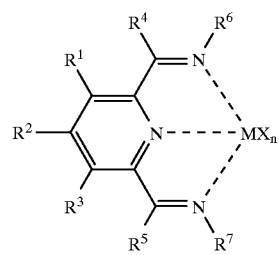

(II)

with ethylene and:
(a) a first compound W, which is a neutral Lewis acid capable of abstracting $X^-$ and alkyl group or a hydride group from M to form $WX^-$, $WR^{20}$ or WH and which is also capable of transferring an alkyl group or a hydride to M, provided that $WX^-$ is a weakly coordinating anion; or
(b) a combination of a second compound which is capable of transferring an alkyl or hydride group to M and a third compound which is a neutral Lewis acid which is capable of abstracting $X^-$, a hydride or an alkyl group from M to form a weakly coordinating anion;

wherein:
M is Co or Fe;
each X is an anion;
n is 1, 2 or 3 so that the total number of negative charges on said anion or anions is equal to the oxidation state of said Fe or Co atom present in (II);
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group, or substituted hydrocarbyl;
$R^6$ and $R^7$ are aryl or substituted aryl; and
$R^{20}$ is alkyl.

2. A process for the polymerization of ethylene, comprising contacting, at a temperature of about −100° C. to about +200° C., a Co[II], Co[III], Fe[II] or Fe[III] complex of a tridentate ligand of the formula

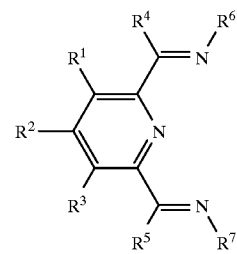

(I)

with ethylene, wherein:
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group or substituted hydrocarbyl; and $R^6$ and $R^7$ are aryl or substituted aryl;

and provided that said Co[II], Co[III], Fe[II] or Fe[III] atom also has an empty coordination site or bonded to it a ligand that may be displaced by said ethylene, and a ligand that may add to said ethylene.

3. The process as recited in claim 1 or 2 wherein:

$R^6$ is

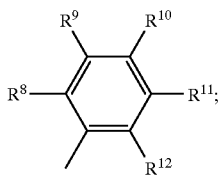

(X)

$R^7$ is

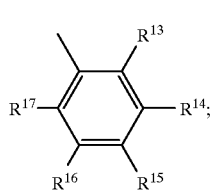

(XI)

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

4. The process as recited in claim 3 wherein:

$R^1$, $R^2$ and $R^3$ are hydrogen;

$R^9$, $R^{10}$, $R^{11}$, $R^{14}$, $R^{15}$ and $R^{16}$ is each independently halogen, alkyl containing 1 to 6 carbon atoms, or hydrogen;

$R^8$ and $R^{13}$ is each independently halogen, phenyl or alkyl containing 1 to 6 carbon atoms;

$R^{12}$ and $R^{17}$ is each independently halogen, phenyl, hydrogen, or alkyl containing 1 to 6 carbon atoms; and $R^4$ and $R^5$ are each independently hydrogen or alkyl containing 1 to 6 carbon atoms.

5. The process as recited in claim 4 wherein $R^9$, $R^{10}$, $R^{11}$, $R^{14}$, $R^{15}$, and $R^{16}$ are each hydrogen.

6. The process as recited in claim 4 wherein $R^8$, $R^{12}$, $R^{13}$, and $R^{17}$ are each alkyl containing 1–6 carbon atoms.

7. The process as recited in claim 4 wherein $R^4$ and $R^5$ are each hydrogen or methyl.

8. The process as recited in claim 4 wherein:

$R^1$, $R^2$, $R^3$, $R^9$, $R^{11}$, $R^{14}$ and $R^{16}$ are hydrogen, and $R^4$, $R^5$, $R^8$, $R^{10}$, $R^{12}$, $R^{13}$, $R^{15}$ and $R^{17}$ are methyl; or $R^1$, $R^2$, $R^3$, $R^9$, $R^{10}$, $R^{11}$, $R^{14}$, $R^{15}$ and $R^{16}$ are hydrogen, $R^8$ and $R^{13}$ are chloro, and $R^4$, $R^5$, $R^{12}$ and $R^{17}$ are methyl; or $R^1$, $R^2$, $R^3$, $R^4$, $R^5$, $R^9$, $R^{10}$, $R^{11}$, $R^{12}$, $R^{14}$, $R^{15}$, $R^{16}$, and $R^{17}$ are hydrogen, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are methylthio, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are 1-imidazolyl, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are methyl, and $R^8$, $R^{12}$, $R^{13}$ and $R^{17}$ are i-propyl; or $R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are t-butyl.

9. The process as recited in claim 4 wherein X is chloride, bromide or tetrafluoroborate.

10. The process as recited in claim 4 wherein said neutral Lewis acid is an alkyl aluminum compound.

11. The process as recited in claim 10 wherein said alkyl aluminum compound is polymethylaluminoxane.

12. The process as recited in claim 4 wherein said temperature is about −50° C. to about 100° C.

13. The process as recited in claim 1 or 2 wherein a pressure of said ethylene is about atmospheric pressure to about 275 MPa.

14. The process as recited in claim 1 or 2 wherein polyethylene with an average DP of 40 or more is produced.

15. The process as recited in claim 1 wherein $R^{20}$ contains 1 to 4 carbon atoms.

16. The process as recited in claim 1 wherein said compound is or becomes part of a heterogeneous catalyst on a solid support.

17. The process as recited in claim 16 carried out in the gas phase or liquid phase.

18. The process as recited in claim 2 wherein said complex is or becomes part of a heterogeneous catalyst on a solid support.

19. The process as recited in claim 18 carried out in the gas or liquid phase.

20. A compound of the formula

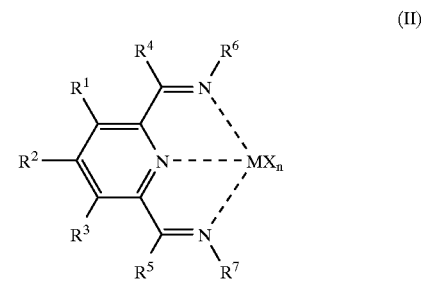

(II)

wherein:

M is Co or Fe;

each X is an anion;

n is 1, 2 or 3, so that the total number of negative charges on said anion or anions is equal to the oxidation state of said Fe or Co atom present in (II);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ is

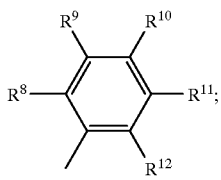
(X)

$R^7$ is

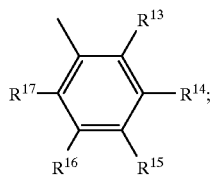
(XI)

$R^8$ and $R^{13}$ are each independently hydrocarbyl, substituted hydrocarbyl or a functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

21. The compound as recited in claim 20 wherein:
$R^1$, $R^2$ and $R^3$ are hydrogen;
$R^9$, $R^{10}$, $R^{11}$, $R^{14}$, $R^{15}$, and $R^{16}$ is each independently halogen, alkyl containing 1 to 6 carbon atoms, or hydrogen;
$R^8$, $R^{13}$, $R^{12}$ and $R^{17}$ is each independently halogen, phenyl, or alkyl containing 1 to 6 carbon atoms; and
$R^4$ and $R^5$ are each independently hydrogen or alkyl containing 1 to 6 carbon atoms.

22. The compound as recited in claim 20 or 21 wherein $R^9$, $R^{10}$, $R^{11}$, $R^{14}$, $R^{15}$, and $R^{16}$ are each hydrogen.

23. The compound as recited in claim 20 or 21 wherein $R^8$, $R^{12}$, $R^{13}$, and $R^{17}$ are each alkyl containing 1–6 carbon atoms.

24. The compound as recited in claim 23 $R^4$ and $R^5$ are each hydrogen or methyl.

25. The compound as recited in claim 20 wherein:
$R^1$, $R^2$, $R^3$, $R^9$, $R^{11}$, $R^{14}$ and $R^{16}$ are hydrogen, and $R^4$, $R^5$, $R^8$, $R^{10}$, $R^{12}$, $R^{13}$, $R^{15}$ and $R^{17}$ are methyl; or $R^1$, $R^2$, $R^3$, $R^9$, $R^{10}$, $R^{11}$, $R^{14}$, $R^{15}$ and $R^{16}$ are hydrogen, $R^8$ and $R^{13}$ are chloro, and $R^4$, $R^5$, $R^{12}$ and $R^{17}$ are methyl; or $R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are phenyl; or $R^1$, $R^2$, $R^3$, $R^4$, $R^5$, $R^9$, $R^{10}$, $R^{11}$, $R^{14}$, $R^{15}$, and $R^{16}$ are hydrogen, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are methylthio, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are 1-imidazolyl, and $R^8$, $R^{12}$, $R^{13}$ and $R^{17}$ are i-propyl; or $R^1$, $R^2$, $R^3$, $R^9$, $R^{10}$, $R^{11}$, $R^{14}$, $R^{15}$ and $R^{16}$ are hydrogen, $R^4$ and $R^5$ are methyl, and $R^8$, $R^{12}$, $R^{13}$ and $R^{17}$ are i-propyl; or $R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are t-butyl.

26. A compound of the formula

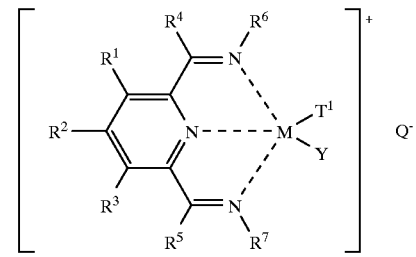
(VII)

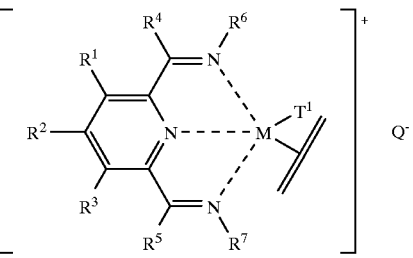
(XII)

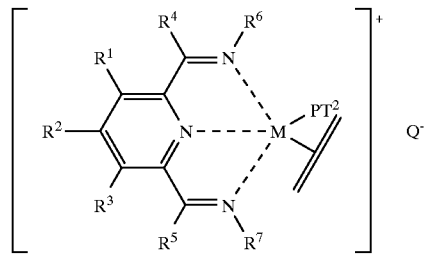
(IX)

wherein:

M is Co or Fe;

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ and $R^7$ are aryl or substituted aryl;

$T^1$ is hydride or alkyl or any other anionic ligand into which ethylene can insert;

Y is a neutral ligand capable of being displaced by ethylene or a vacant coordination site;

Q is a relatively non-coordinating anion;

P is a divalent (poly)ethylene group of the formula —$(CH_2CH_2)_x$— wherein x is an integer of 1 or more; and $T^2$ is an end group.

27. The compound as recited in claim 26 wherein:

R$^6$ is

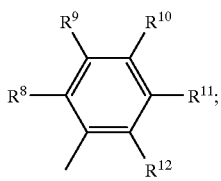
(X)

R$^7$ is

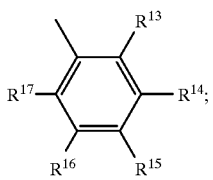
(XI)

R$^8$ and R$^{13}$ are each independently hydrocarbyl, substituted hydrocarbyl or an inert functional group;

R$^9$, R$^{10}$, R$^{11}$, R$^{14}$, R$^{15}$ and R$^{16}$ are each independently hydrogen, hydrocarbyl, substituted hydrocarbyl or an inert functional group;

R$^{12}$ and R$^{17}$ are each independently hydrogen, hydrocarbyl, substituted hydrocarbyl or an inert functional group;

and provided that any two of R$^8$, R$^9$, R$^{10}$, R$^{11}$, R$^{12}$, R$^{13}$, R$^{14}$, R$^{15}$, R$^{16}$ and R$^{17}$ that are vicinal to one another, taken together may form a ring.

28. The compound as recited in claim 27 wherein:

R$^1$, R$^2$ and R$^3$ are hydrogen;

R$^9$, R$^{10}$, R$^{11}$, R$^{14}$, R$^{15}$ and R$^{16}$ is each independently halogen, alkyl containing 1 to 6 carbon atoms, or hydrogen;

R$^8$ and R$^{13}$ is each independently halogen, phenyl or alkyl containing 1 to 6 carbon atoms;

R$^{12}$ and R$^{17}$ is each independently halogen, phenyl, hydrogen, or alkyl containing 1 to 6 carbon atoms; and R$^4$ and R$^5$ are each independently hydrogen or alkyl containing 1 to 6 carbon atoms.

29. The compound as recited in claim 28 wherein R$^9$, R$^{10}$, R$^{11}$, R$^{14}$, R$^{15}$ and R$^{16}$ are each hydrogen.

30. The compound as recited in claim 26 which is (VII).

31. The compound as recited in claim 26 which is (XII).

32. The compound as recited in claim 26 which is (IX).

33. A process for the polymerization of ethylene, comprising, contacting, at a temperature of about −100° C. to about +200° C., ethylene and a compound of the formula

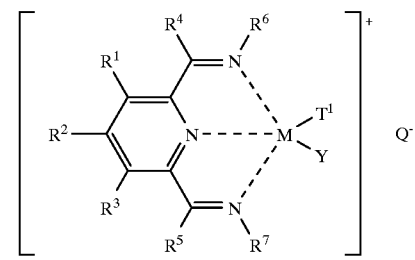
(VII)

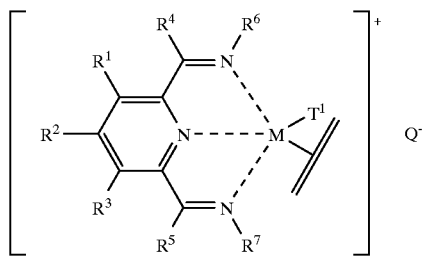
(XII)

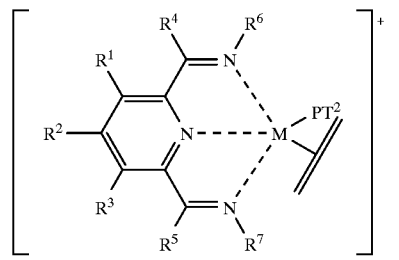
(IX)

wherein:

M is Co or Fe;

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl, an inert functional group or substituted hydrocarbyl;

R$^6$ and R$^7$ are aryl or substituted aryl;

T$^1$ is hydride or alkyl or any other anionic ligand into which ethylene can insert;

Y is a neutral ligand capable of being displaced by ethylene or a vacant contamination site;

Q is a relatively non-coordinating anion;

P is a divalent (poly)ethylene group of the formula —(CH$_2$CH$_2$)$_x$— wherein x is an integer of 1 or more; and T$^2$ is an end group.

34. The process as recited in claim 33 wherein said compound is (VII).

35. The process as recited in claim 33 wherein said compound is (IX).

36. The process as recited in claim 33 wherein said compound is (XII).

37. The process as recited in claim 33 wherein:

$R^6$ is

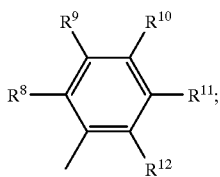
(X)

$R^7$ is

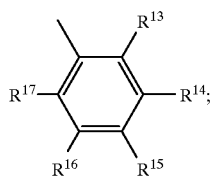
(XI)

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

38. The process as recited in claim 37 wherein:

$R^1$, $R^2$ and $R^3$ are hydrogen;

$R^9$, $R^{10}$, $R^{11}$, $R^{14}$, $R^{15}$ and $R^{16}$ is each independently halogen, alkyl containing 1 to 6 carbon atoms, or hydrogen;

$R^8$ and $R^{13}$ is each independently halogen, phenyl or alkyl containing 1 to 6 carbon atoms;

$R^{12}$ and $R^{17}$ is each independently halogen, phenyl, hydrogen, or alkyl containing 1 to 6 carbon atoms; and $R^4$ and $R^5$ are each independently hydrogen or alkyl containing 1 to 6 carbon atoms.

39. The process as recited in claim 38 wherein $R^9$, $R^{10}$, $R^{11}$, $R^{14}$, $R^{15}$, and $R^{16}$ are each hydrogen.

40. The process as recited in claim 33, 34, 35 or 36 wherein said temperature is about –50° C. to about 100° C.

41. The process as recited in claim 33, 34, 35 or 36 wherein a pressure of said ethylene is about atmospheric pressure to about 275 MPa.

42. The process as recited in claim 33 wherein polyethylene with an average DP of 40 or more is produced.

43. The process as recited in claim 33 wherein (VI), (IX) or (XII) is part of a heterogeneous catalyst on a solid support.

44. The process as recited in claim 43 carried out in the gas or liquid phase.

45. The process as recited in claim 16, 18 or 43 wherein said solid support is silica or alumina.

* * * * *